(12) United States Patent
Hoelscher et al.

(10) Patent No.: US 11,634,659 B2
(45) Date of Patent: Apr. 25, 2023

(54) FRAGRANCES WITH ROSE SCENT

(71) Applicant: SYMRISE AG, Holzminden (DE)

(72) Inventors: Bernd Hoelscher, Halle (DE); Vijayanand Chandrasekaran, Holzminden (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 17/261,444

(22) PCT Filed: Jul. 23, 2018

(86) PCT No.: PCT/EP2018/069950
§ 371 (c)(1),
(2) Date: Jan. 19, 2021

(87) PCT Pub. No.: WO2020/020434
PCT Pub. Date: Jan. 30, 2020

(65) Prior Publication Data
US 2021/0324300 A1 Oct. 21, 2021

(51) Int. Cl.
| C11D 3/50 | (2006.01) |
|---|---|
| C11B 9/00 | (2006.01) |
| A61K 8/35 | (2006.01) |
| A61Q 5/02 | (2006.01) |
| C07C 29/14 | (2006.01) |
| C07C 35/08 | (2006.01) |
| C07C 47/32 | (2006.01) |
| C07C 49/403 | (2006.01) |
| C11D 3/00 | (2006.01) |
| C11D 3/20 | (2006.01) |
| C11D 17/06 | (2006.01) |

(52) U.S. Cl.
CPC .............. *C11B 9/0034* (2013.01); *A61K 8/35* (2013.01); *A61Q 5/02* (2013.01); *C07C 29/14* (2013.01); *C07C 35/08* (2013.01); *C07C 47/32* (2013.01); *C07C 49/403* (2013.01); *C11D 3/001* (2013.01); *C11D 3/2024* (2013.01); *C11D 17/06* (2013.01)

(58) Field of Classification Search
CPC .............................. C07C 35/08; C11B 9/0034
See application file for complete search history.

(56) References Cited

U.S. PATENT DOCUMENTS

| 4,041,083 A | 8/1977 | Gradeff et al. |
|---|---|---|
| 2006/0089413 A1 | 4/2006 | Schmaus et al. |
| 2008/0070825 A1 | 3/2008 | Bertram et al. |
| 2010/0130397 A1 | 5/2010 | Reckziegel et al. |

FOREIGN PATENT DOCUMENTS

| DE | 2744134 A1 | 4/1978 |
|---|---|---|
| EP | 2168570 A2 | 3/2010 |
| EP | 2193785 A2 | 6/2010 |
| JP | S49-11851 A | 2/1974 |
| JP | S53-44506 A | 4/1978 |
| JP | 2008514673 A | 5/2008 |
| WO | WO-01/76572 A2 | 10/2001 |
| WO | WO-02/15686 A1 | 2/2002 |
| WO | WO-2005/107692 A1 | 11/2005 |
| WO | WO-2005/123101 A1 | 12/2005 |
| WO | WO-2006/015954 A1 | 2/2006 |
| WO | WO-2006/045760 A1 | 5/2006 |
| WO | WO-2006/053912 A1 | 5/2006 |
| WO | WO-2007/009982 A1 | 1/2007 |
| WO | WO-2007/042472 A1 | 4/2007 |
| WO | WO-2007/060256 A2 | 5/2007 |
| WO | WO-2007/110415 A2 | 10/2007 |
| WO | WO-2007/128723 A1 | 11/2007 |

(Continued)

OTHER PUBLICATIONS

V. M. Andreev et al., Oil and Fat Industry, 1974, Issue 10, pp. 31-33. No month available. Professional English translation (Year: 1974).*

(Continued)

*Primary Examiner* — Charles I Boyer

(74) *Attorney, Agent, or Firm* — Marshall, Gerstein & Borun LLP

(57) ABSTRACT

The present invention primarily concerns the use of compounds of the following formula (I)

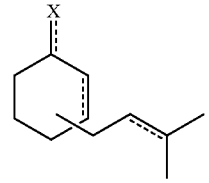

Formula I wherein X represents an oxygen atom, a —CHO, an —OH, or a —CH$_2$OH group, a single bond or a double bond is present at the respective location of one of the dotted lines, at least one double bond is present when X is an OH group, and the 3-isopentyl or 3-isopent-2-enyl residue is connected to the ring in the ortho, meta, or para position to the X group, as perfuming and/or flavouring agents.

The invention further relates to fragrance and flavour compositions containing one or more of these compounds, perfumed or flavoured articles comprising one or more of these compounds and corresponding processes for imparting, modifying and/or enhancing certain odour notes.

16 Claims, No Drawings

(56) References Cited

FOREIGN PATENT DOCUMENTS

| | | |
|---|---|---|
| WO | WO-2008/046676 A1 | 4/2008 |
| WO | WO-2008/046791 A1 | 4/2008 |
| WO | WO-2008/046795 A1 | 4/2008 |

OTHER PUBLICATIONS

Arctander, Perfume and Flavor Materials, vol. I and II, Montclair, N. J. (1969), Table of Contents.

Bauer et al., Common Fragrance and Flavor Materials, 4th Edition, Wiley-VCH, Weinheim (2001), Table of Contents.

Descoins et al., "No. 310.—Transposition homoallylique avec participation II.—Isomerisation acide des [(pentene-4" yl)-2']. cyclopropy1.2 propanols-2 (b) (cis et trans) (*) (**)—[Homoallylic rearrangement with participating groups]" Bulletin de la Societe Chimique de France, 5:1816-1822 (1970).

Feringa et al., "Copper-Catalyzed Asymmetric Conjugate Addition of Grignard Reagents to Cyclic Enones," Proceedings of RGE National Academy of Sciences, 101 (16):5834-5838 (2004).

Hartung et al., "(Schiff-base)vanadium(V) Complex-Catalyzed Oxidations of Susbstituted Bis9homoallylic) Alcohols—Stereoselective Synthesis of Functionalized Tetrahydrofurans," Eur. J. Org. Chern., 2003(23):2388-2408 (2003).

International Search Report and Written Opinion for Application No. PCT/EP2018/069950, dated Apr. 10, 2019.

Kaku et al., "A Facile and Practical Method of Preparing Optically Active a-monosubstituted Cycloalkanones by Thermodynamically Controlled Deracemization," Tetrahedron 66(48):9450-9455 (2010).

Office Action and English Translation from Japanese Application No. 2021-503768 dated Mar. 7, 2022.

Laing et al., Chem. Senses (2003) 28: pp. 57-69.

Genva et al. Is It Possible to Predict the Odor of a Molecule on the Basis of its Structure?, Int. J. al of Mol. Sci. 20(3018): 16 pages (2019).

Leitereg et al., J. Agr. Food Chem. (1971), 19(4) pp. 785-787.

Andreev et al., "Recovery Products of 2- (3-Methyl-2-Butenyl)-Cyclohexanone", Oil and Fat Industry, 10:31-33 (1974).

Office Action and English Translation from Chinese Application No. 2018800959630 dated Oct. 25, 2022.

\* cited by examiner

FRAGRANCES WITH ROSE SCENT

CROSS-REFERENCE TO RELATED APPLICATIONS

This is a U.S. National Phase of International Application No. PCT/EP2018/069950, filed Jul. 23, 2018, the content of which is incorporated herein by reference.

The present invention relates primarily to the use of compounds of the following formula (I) as perfuming and/or flavouring agents. The invention further relates to fragrance and/or flavour compositions containing one or more of these compounds, perfumed and flavoured articles comprising one or more of these compounds and corresponding processes for imparting, modifying and/or enhancing certain odour and/or taste notes.

In US 2010/0130397, for example, the use of 4-isoamyl cyclohexanol as a flavoring agent is described.

Despite the large number of existing fragrances and flavors, there is still a general need for new fragrances and flavors in the perfume and flavor industry. For example, there is a need for fragrance or flavour substances that are able (in fragrance or flavour compositions) to create other interesting notes in addition to a primary fragrance or taste note and to expand the possibilities of the perfumer with their novel or original olfactory properties. In particular, there is an interest in olfactory and/or aromatic substances with scents, which are able to form a harmonious combination with floral and/or fruity scents and/or aromatic substances. Preferably, the different olfactory aspects and notes should be superimposed to create an overall complex olfactory impression.

For the creation of novel compositions, there is a constant need for fragrances and/or flavors with special sensory properties, which are suitable to serve as a basis for the composition of novel perfumes with complex sensory character. Preferred sought-after fragrance and/or flavour substances should have, in addition to a specific note, other notes and aspects that give them character and complexity.

The search for suitable rose-like substances, which led to the present invention, was complicated by the following facts:
i) the mechanisms of olfactory perception are not sufficiently known
ii) the relationships between the special olfactory perception on the one hand and the chemical structure of the associated olfactory and/or aromatic substance on the other hand have not been sufficiently researched;
iii) Often, even minor changes in the structural composition of a known fragrance and/or flavoring agent cause strong changes in the sensory properties and affect the compatibility for the human organism.

The success of the search for suitable fragrances and/or flavour substances therefore strongly depends on the intuition of the searcher.

The primary task now was to find fragrance and/or flavour compounds with an interesting, preferably complex, and original sensory profile and which are suitable as fragrance or flavour compounds for use in perfumery.

Within the scope of the present invention, the search was directed in particular at substances which are capable of exhibiting or mediating, modifying and/or intensifying one, several or all of the notes green, herbaceous, fresh, fruity, floral, woody, sweet, earthy, fatty, metallic and balsamic. In particular, substances should be found with notes that preferably have at least one of the following notes: floral and/or fruity and preferably also have a rose-like smell or can convey a rose note.

The sought-after substances should enable the production of novel olfactory and/or aromatic compositions with special olfactory notes and aspects. It would be advantageous to use substances that are particularly suitable for combination with other fragrances and/or flavors that have a woody and/or floral and/or fruity note.

In addition, the fragrances and/or flavouring substances fulfilling this primary task should preferably have additional positive secondary properties beyond their primary, i.e. olfactory, properties, such as have a high stability under certain application conditions, a high yield, good adhesion, high substantivity, odor-enhancing properties (so-called booster or enhancer effect) and/or, in combination with other fragrances and/or flavors, round off their naturalness, freshness, fullness, (radiant) power and/or radiance, so that remarkable sensory effects can be achieved.

A further task of the invention relates to the production of such novel fragrances and/or flavours in any form, their isomers, as well as mixtures thereof.

Another task is the provision of new compounds for use as fragrances and flavorings, of preferred mixtures, and of consumer products containing these mixtures and their production.

These tasks are solved by the combinations of features defined in the main claims. Preferred embodiments are the subject of the subclaims.

SUMMARY OF THE INVENTION

The invention relates in a first aspect to the use of a compound of formula (I)

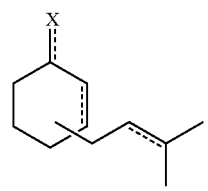

Formula I wherein X represents an oxygen atom, a —CHO, an —OH, or a —CH$_2$OH group, a single bond or a double bond is present at the respective position of one of the dotted lines, at least one double bond is present when X is an OH group, and wherein the 3-isopentyl or 3-isopent-2-enyl moiety is in ortho-, meta-, or para-position to the X-group is connected to the ring with the proviso that if a double bond is present in the ring, then the 3-isopentyl or 3-isopent-2-enyl radical is directly connected to this double bond as an ortho- or meta-substituent, as a fragrance and/or flavouring agent.

A particularly preferred alternative here and below is the use of a compound of formula (Ia),

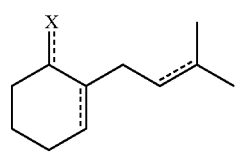

Formula Ia wherein X represents an oxygen atom, a —CHO, an —OH, or a —CH$_2$OH group, a single bond or a double bond is present at the respective position of one of the dotted lines, and when X is an OH group, at least one double bond is present, as a fragrance and/or flavouring agent.

Another particularly preferred alternative here and below is the use of a compound of formula (Ib),

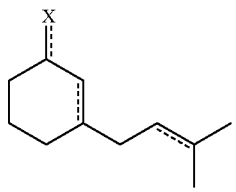

Formula Ib wherein X represents an oxygen atom, a —CHO, an —OH, or a —CH$_2$OH group, a single bond or a double bond is present at the respective position of one of the dotted lines, and when X is an OH group, at least one double bond is present, as a fragrance and/or flavouring agent.

An alternative particularly preferred alternative here and below is the use of a compound of formula (Ic),

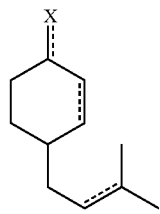

Formula Ic wherein X represents an oxygen atom, a —CHO, an —OH, or a —CH$_2$OH group, a single bond or a double bond is present at the respective position of one of the dotted lines, and when X is an OH group, at least one double bond is present, as a fragrance and/or flavouring agent.

A particularly preferred alternative of formula (I), formula (Ia), formula (Ib), and/or formula (Ic) is here and below that the double bond is a "C=C" double bond.

The use of the following molecular variants as fragrance and/or flavoring agents is also preferred:

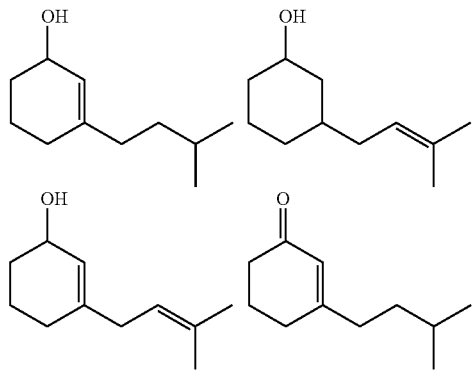

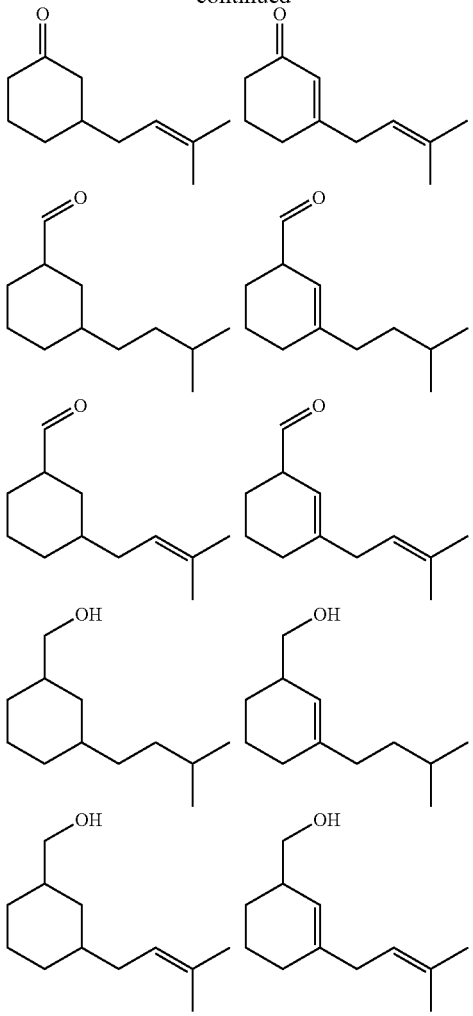

The molecule variants are each shown with the meta substituent, but the substituent can also be bound preferentially in the ortho or para position, as for example in 4-isopentyl-cyclohex-2-en-1-ol, 2-isopentylcyclohex-2-en-1-ol, 4-isopentylcyclohex-2-en-1-one, or 2-isopentylcyclohex-2-en-1-one. Therefore, all sample formulas shown above are also preferred with ortho- or para-substituent.

The compounds of formula (I), of formula (Ia), of formula (Ib), and/or of formula (Ic) have completely independent olfactory properties which clearly stand out from and even exceed those of known fragrances and/or flavours. The suitability of the compounds of formula (I), of formula (Ia), of formula (Ib), and/or of formula (Ic) as fragrance and/or flavour substances has not been known so far. It is therefore particularly surprising that these valuable fragrance and/or flavour compounds with interesting and complex olfactory properties could be found.

The use of the compounds according to the invention as rose-scented and/or aromatic substances is particularly preferred.

A preferred variant of the present invention concerns the use of a compound of formula (I), formula (Ia), formula (Ib), and/or formula (Ic), wherein X represents an oxygen atom, a —CHO, an —OH, or a —CH$_2$OH group, and at least one double bond is present at the respective location of one of the dotted lines, as a perfuming and/or flavouring agent.

The use of the following molecule variants as fragrance and/or flavoring agents is particularly preferred

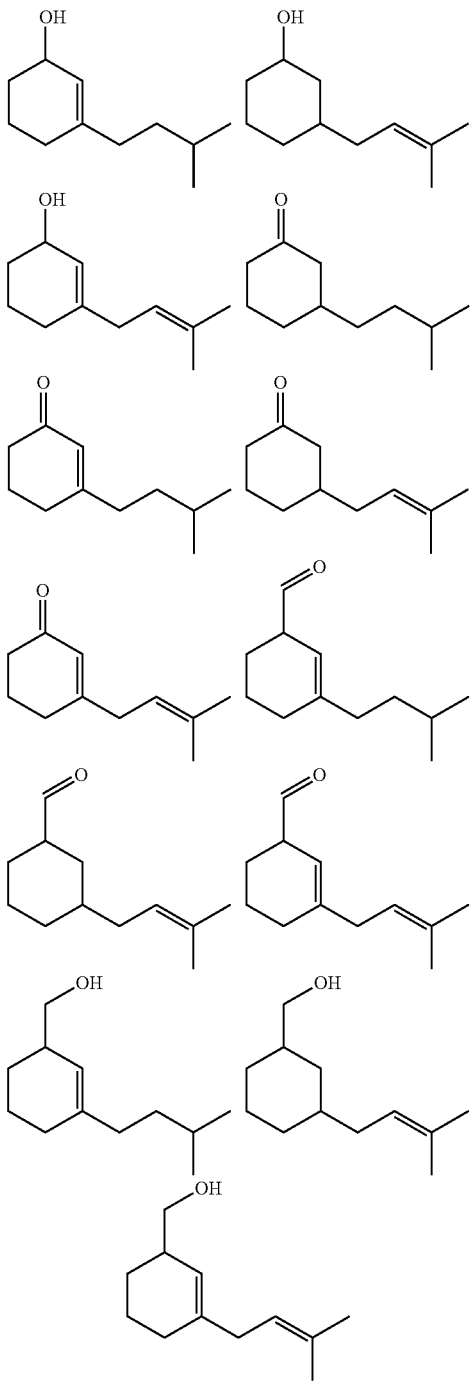

The molecule variants are each preferred with the meta substituent, in particular, the substituent can also be bound preferentially in the ortho or para position, as is the case with 4-isopentylcyclohex-2-en-1-ol, 2-isopentylcyclohex-2-en-1-ol, 4-isopentylcyclohex-2-en-1-one, or 2-isopentylcyclohex-2-en-1-one. All of the above shown example formulas are therefore also preferred with ortho- or para-substituent.

These compounds are particularly preferred because they have a stronger rosy and fruity odor profile. They also have positive secondary properties, such as high stability under certain application conditions.

An alternative preferred variation of the present invention concerns compounds of formula (I), formula (Ia), formula (Ib), and/or formula (Ic), wherein X represents an oxygen atom, a —CHO, an —OH, or a —CH$_2$OH group, at the respective location of one of the dotted lines in the ring and in the isobutyl side chain a double bond is present, as a fragrance and/or flavouring agent.

A further preferred embodiment of the present invention concerns compounds of formula (I), formula (Ia), formula (Ib), and/or formula (Ic), wherein X represents an oxygen atom, a —CHO, an —OH, or a —CH$_2$OH group, a single bond or a double bond being present at the location of one of the dotted lines, and wherein the compound is not 2-(3-methylbutyl)cyclohexan-1-ol, 2-(3-methylbutyl)cyclohexan-1-one 3-(3-methylbutyl)cyclohexan-1-ol, 3-(3-methylbutyl)cyclohexan-1-one 4-(3-methylbutyl)cyclohexan-1-ol, or 4-(3-methylbutyl)cyclohexan-1-one, as fragrance and/or flavoring agent.

The use of the following molecule variants as fragrance and/or flavoring agents is particularly preferred

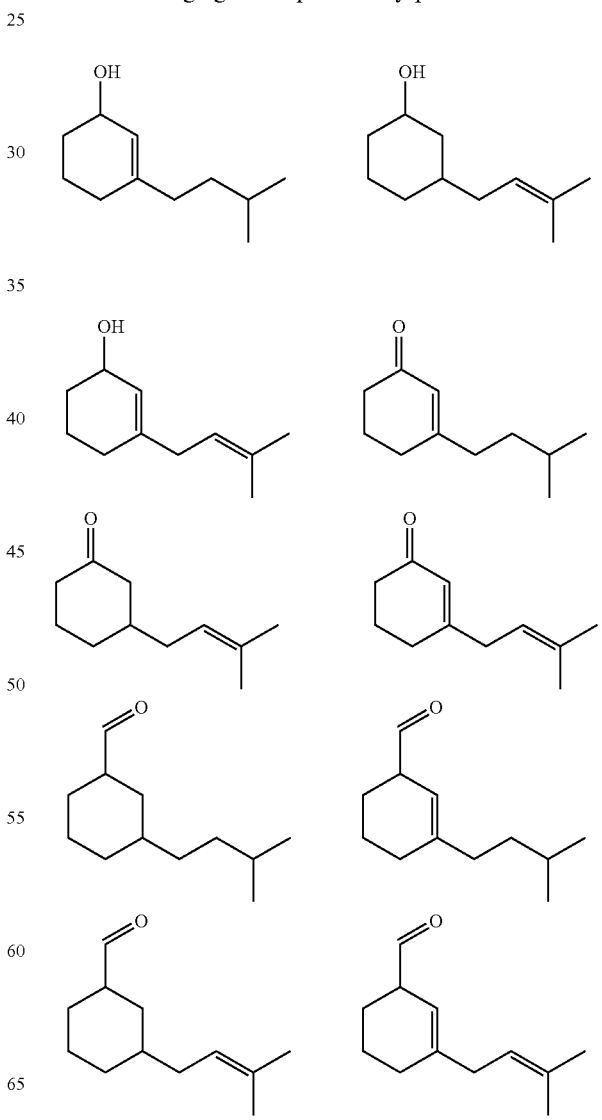

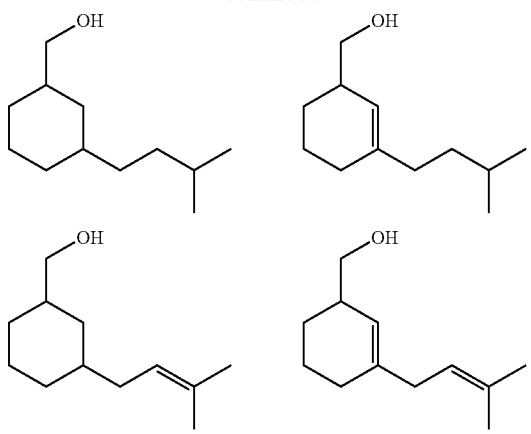

Molecular variants are preferably shown with the meta substituent, the substituent can also be bound in the ortho or para position, as for example in 4-isopentylcyclohex-2-en-1-ol, 2-isopentylcyclohex-2-en-1-ol, 4-isopentylcyclohex-2-en-1-one, or 2-isopentylcyclohex-2-en-1-one. All the example formulas shown above are therefore also preferred with ortho- or para-substituent.

An alternative preferred embodiment of the present invention concerns compounds of formula (I), formula (Ia), formula (Ib), and/or formula (Ic), wherein X represents an oxygen atom, a —CHO, an —OH, or a —CH$_2$OH group, at the respective location of one of the dotted lines either in the ring or in the isobutyl side chain a double bond is present, as a perfuming and/or flavouring agent.

These compounds are particularly preferred because they can modify and/or enhance the fruity, floral and woody notes particularly well.

The invention concerns in a second aspect, compounds of formula (II),

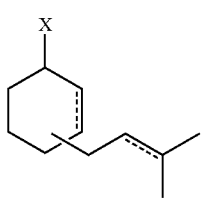

Formula II wherein, X represents a —CHO or a —CH$_2$OH group, a single bond or a double bond is present at the location of one of the dotted lines, and wherein the 3-isopentyl or 3-isopent-2-enyl moiety is connected to the ring at a position ortho, meta, or para to the X group with the proviso that if a double bond is present in the ring, then the 3-isopentyl or 3-isopent-2-enyl moiety is directly connected to said double bond as an ortho or meta substituent.

The preferred embodiments and structural variants of the first aspect of the present invention also apply in each case to the second aspect and can also be combined with the basic structure according to Formula II.

In this context, a further preferred form of the present invention concerns the following molecule variants:

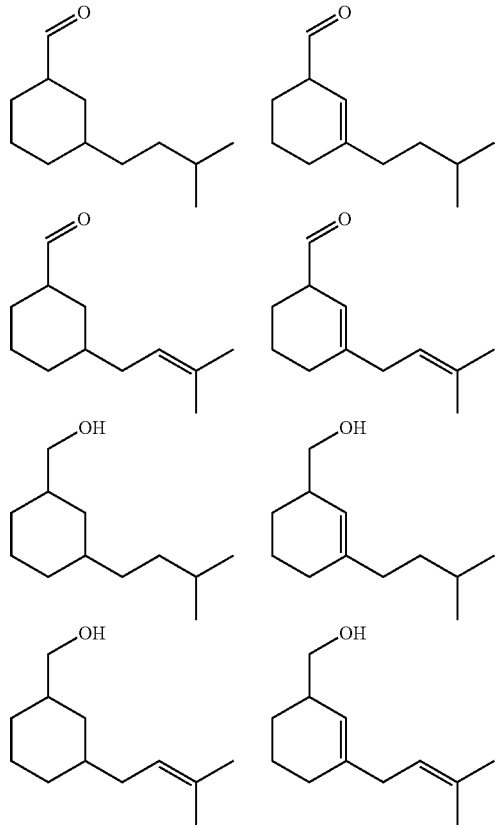

The compounds of formula (II) have an additional "carbon" atom between the ring and the heteroatom, making them particularly suitable as fragrances. In addition, the compounds according to the invention convince by an extraordinarily good adhesion (long lasting) and a high substantivity.

An alternative preferred configuration of the present invention concerns compounds of formula (II), wherein X represents a —CHO or a —CH$_2$OH group, a single bond is present at the location of the dotted lines and the 3-isopentyl or 3-isopent-2-enyl radical is in ortho-, meta, or para to the X group, provided that if a double bond is present in the ring, then the 3-isopentyl or 3-isopent-2-enyl moiety is directly attached to that double bond as an ortho- or meta-substituent.

A preferred feature of the present invention concerns the use of a compound of formula (II),

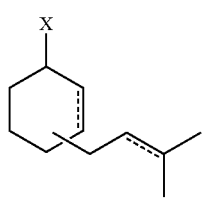

Formula II wherein X represents a —CHO or a —CH$_2$OH group, a single bond or a double bond is present at the location of the dotted lines, and the 3-isopentyl or 3-isopent-2-enyl radical is in ortho, meta-, or para position to the X group is connected to the ring, with the proviso that if a double bond is present in the ring, then the 3-isopentyl or 3-isopent-2-enyl moiety is directly attached to this double bond as an ortho- or meta-substituent, as a fragrance and/or flavouring agent.

The use of the following molecule variants as fragrance and/or flavoring agents is particularly preferred

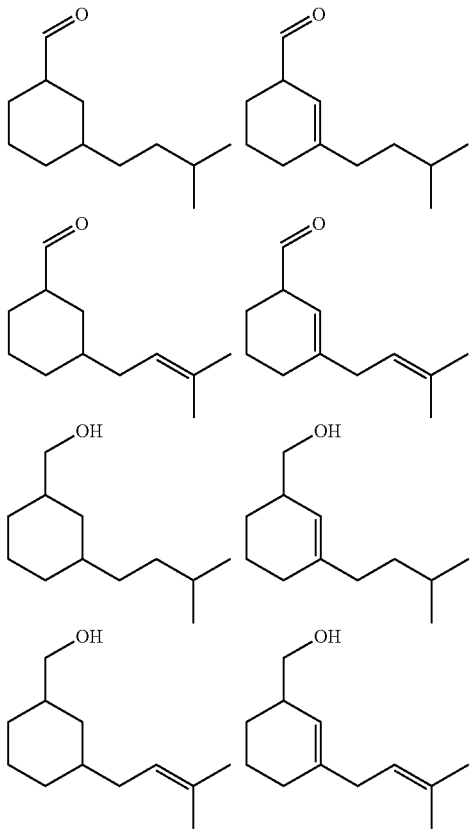

These molecule variants are preferably shown with the meta substituent, the substituent can also be bound in the ortho or para position, as for example in 2-isopentylcyclohex-2-ene-1-carbaldehydes, 4-isopentylcyclohex-2-ene-1-carbaldehydes, 2-(3-methylbut-2-enyl)cyclohexane carbaldehyde, 4-(3-methylbut-2-enyl)cyclohexane carbaldehydes, [2-(3-methylbut-2-enyl)cyclohexyl]methanol, [4-(3-methylbut-2-enyl)cyclohexyl]methanol, (2-isopentylcyclohex-2-en-1-yl)methanol or (4-isopentylcyclohex-2-en-1-yl)methanol. All of the above shown example formulas are therefore also preferred with ortho- or para-substituent.

The compounds of formula (II) have an outstanding and unique olfactory profile, including rosy and floral notes. In addition, the compounds according to the invention convince by an exceptionally good adhesion (long lasting) and a high substantivity.

An alternative preferred configuration of the present invention relates to compounds of formula (II), wherein X represents a —CHO or a —CH$_2$OH group, a single bond is present at the location of the dotted lines and the 3-isopentyl or 3-isopentenyl residue is connected to the ring in the ortho, meta or para position relative to the X group, as perfuming and/or flavouring agent.

The use of the following molecular variants as fragrance and/or flavoring agents is particularly preferred: 2-isopentyl cyclohexane carb aldehydes, (2-isopentylcyclohexyl)methanol, 3-isopentylcyclohexane carbaldehydes, (3-isopentylcyclohexyl)methanol, 4-isopentylcyclohexane carbaldehydes and (4-isopentyl cyclohexyl)methanol.

These compounds are particularly preferred because they have odor-enhancing properties (so-called booster or enhancer effect) and/or, in combination with other fragrances and/or flavors, round out their naturalness, freshness, fullness, (radiance) power and/or radiance.

A further alternative preferred configuration of the present invention concerns the use of a compound of the formula (II), wherein X represents a —CHO, or a —CH$_2$OH group, at least one double bond is present at the location of one of the dotted lines and the 3-isopentyl or 3-isopentenyl residue is connected to the ring in the ortho, meta or para position to the X group, as perfuming and/or flavouring agent.

The use of the following molecule variants as fragrance and/or flavoring agents is particularly preferred

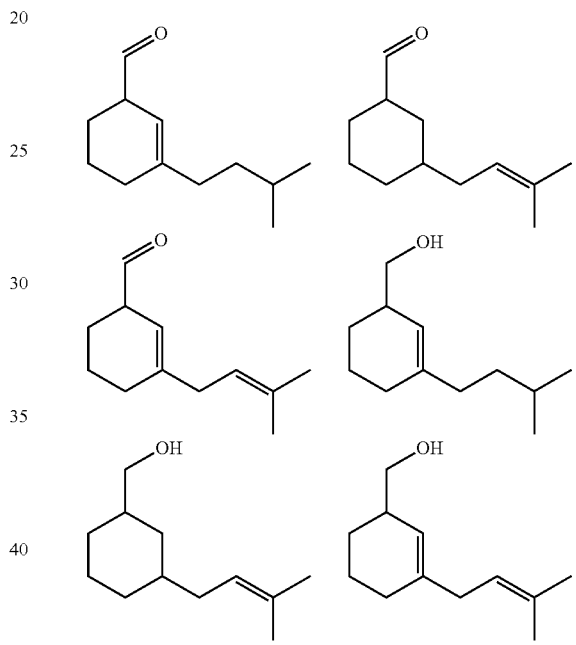

Molecular variants are preferably shown with the meta substituent, the substituent can also be bound in the ortho or para position, as for example in 2-isopentylcyclohex-2-ene-1-carbaldehydes, 4-isopentylcyclohex-2-ene-1-carbaldehydes, 2-(3-methylbut-2-enyl)cyclohexane carbaldehydes, 4-(3-methylbut-2-enyl)cyclohexane carbaldehydes [2-(3-methylbut-2-enyl)cyclohexyl]methanol, [4-(3-methylbut-2-enyl)cyclohexyl]methanol, (2-isopentylcyclohex-2-en-1-yl) methanol or (4-isopentylcyclohex-2-en-1-yl)methanol. All of the example formulas shown above are therefore also preferred with ortho- or para-substituent.

The compounds of formula (I), formula (Ia), formula (Ib), formula (Ic), and/or formula (II) according to the invention or to be used according to the invention may be present in any optically active form, as well as in any mixture of stereoisomers, for example as a mixture of diastereomers or as a racemate.

A preferred variant of the present invention concerns compounds of formula (I), formula (Ia), formula (Ib), formula (Ic), and/or formula (II), in all forms of their cis- or trans-isomers (E/Z isomers) at the 2-, 3-, or 4-position, as well as mixtures thereof.

In a third aspect, the invention relates to the use of a compound of formula (I), formula (Ia), formula (Ib), formula (Ic), and/or formula (II) according to variants according to the invention, as a rose note fragrance.

In a fourth aspect, the invention relates to the use of a compound of formula (I), formula (Ia), formula (Ib), formula (Ic), and/or formula (II) for imparting, modifying and/or enhancing one or more olfactory notes selected from the group consisting of the notes green, herbaceous, fresh, fruity, floral, woody, sweet, earthy, fatty, metallic and balsamic, preferably at least one of the notes green and/or fruity.

A preferred embodiment of the present invention concerns the use of a compound of formula (I), formula (Ia), formula (Ib), formula (Ic), and/or formula (II) according to variants according to the invention for imparting one, two or more olfactory notes selected from the group consisting of the notes green, fresh, fruity and woody.

Preferably, the present invention relates to the use of a compound of formula (I), formula (Ia), formula (Ib), formula (Ic), and/or formula (II) according to variants according to the invention as a perfuming and/or flavouring agent,
i) with a rose note
and/or
ii) for imparting, modifying and/or reinforcing one or more olfactory notes selected from the group consisting of the notes green, herbaceous, fresh, fruity, woody, sweet, earthy, fatty, metallic and balsamic, preferably at least one of the notes green and/or fruity being imparted, modified and/or reinforced.

In a fifth aspect, the invention relates to a perfuming and/or flavouring substance comprising at least one compound of formula (I), formula (Ia), formula (Ib), formula (Ic), and/or formula (II) according to variants according to the invention.

The compounds of the formula (I), the formula (Ia), the formula (Ib), the formula (Ic), and/or the formula (II) are excellently suited for use in fragrance and/or flavour mixtures and/or fragrance and/or flavour compositions due to their olfactory properties. One or more compounds of the formula (I), of the formula (Ia), of the formula (Ib), of the formula (Ic), and/or of the formula (II) can be combined with a large number of other fragrance and/or flavour substances and used in numerous different products and articles. The compounds of the formula (I), the formula (Ia), the formula (Ib), the formula (Ic), and/or the formula (II) can be combined particularly advantageously with other fragrance and/or flavoring substances in different, different proportions to form fragrance and/or flavoring mixtures and/or fragrance and/or flavoring compositions according to the invention.

In a further variant, the invention relates to a fragrance and/or flavouring composition comprising at least one fragrance and/or flavouring substance according to the fifth aspect and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one, further comprising one or more additional fragrance and/or flavouring substances, wherein the or the additional or one, several or all of the fragrances and/or flavouring substances is/are selected from a group consisting of: extracts from natural raw materials, preferably essential oils, creams, absolutes, resins, resinoids, balms, tinctures and/or single fragrances, preferably from the group of (1) hydrocarbons; (2) aliphatic alcohols; (3) aliphatic aldehydes and their acetals; (4) aliphatic ketones and their oximes; (5) aliphatic sulfur-containing compounds; (6) aliphatic nitriles; (7) esters of aliphatic carboxylic acids; (8) acyclic terpene alcohols; (9) acyclic terpene aldehydes and ketones; (10) cyclic terpene alcohols; (11) cyclic terpene aldehydes and ketones; (12) cyclic alcohols; (13) cycloaliphatic alcohols; (14) cyclic and cycloaliphatic ethers; (15) cyclic and macrocyclic ketones; (16) cycloaliphatic aldehydes; (17) cycloaliphatic ketones; (18) esters of cyclic alcohols; (19) esters of cycloaliphatic alcohols; (20) esters of cycloaliphatic carboxylic acids; (21) araliphatic alcohols; (22) esters of araliphatic alcohols and aliphatic carboxylic acids (23) araliphatic ethers; (24) aromatic and araliphatic aldehydes; (25) aromatic and araliphatic ketones; (26) aromatic and araliphatic carboxylic acids and their esters; (27) nitrogen-containing aromatic compounds; (28) phenols, phenyl ethers and phenyl esters; (29) heterocyclic compounds; (30) lactones; and mixtures thereof.

In a sixth aspect, the invention relates to a fragrance and/or flavouring composition comprising at least one compound of formula (III)

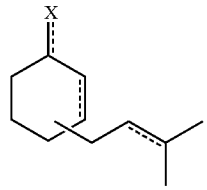

Formula III where
X represents an oxygen atom, a —CHO, an —OH, or a —CH$_2$OH group,
in each case a single bond or a double bond is present at the respective location of one of the dotted lines, and wherein the 3-isopentyl or 3-isopent-2-enyl radical is connected to the ring in the ortho, meta or para position relative to the X group, and at least one further fragrance.

The compounds of the formula (I), the formula (Ia), the formula (Ib), the formula (Ic), the formula (II) and/or the formula (III), which are according to the invention or are to be used according to the invention, are usually used in inventive applications, in a sensory effective amount, i.e. in a total amount in which they develop a sensory effect.

Preferably the inventive or compounds of formula (I), formula (Ia), formula (Ib), formula (Ic), of formula (II) and/or of formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one are used together with other perfumes.

Such fragrance and/or flavouring mixtures and/or fragrance and/or flavouring compositions may be prepared in the usual way, for example by simple mixing or homogenisation of the ingredients. Such further fragrance and/or flavouring substances may be any other fragrance and/or flavouring substances.

In a preferred perfuming and/or flavouring mixture and/or fragrance and/or flavouring composition according to the invention, the weight ratio of the total amount of compounds of the formula (I), the formula (I), the formula (Ia), the formula (Ib), the formula (Ic), the formula (II) and/or the formula (III) preferably in one of the forms indicated above as preferred, to the total amount of other perfuming and/or flavouring substances is in the range from 1:1000 to 1:0.5.

In particular by combining the compounds of the above-mentioned formulae, and in particular formula (I) and formula (III), in variants according to the invention, preferably in one of the forms indicated as preferred, with one or more further perfuming and/or flavouring substances (preferably with a woody, fruity and/or floral smell or taste), interesting new perfuming and/or flavouring mixtures and/or fragrance- and/or flavouring compositions can be produced. In this way it is possible to create mixtures with particularly interesting, natural, new and original notes. Scent and/or flavor compounds that are suitable as (b) component, as described above, of a fragrance and/or flavor composition according to the invention can be found, for example, in S. Arctander, Perfume and Flavor Materials, Vol. I and II, Montclair, N.J. 1969, self-published, or K. Bauer et al., Common Fragrance and Flavor Materials, 4th Edition, Wiley-VCH, Weinheim 2001.

In detail are mentioned: Extracts from natural raw materials such as essential oils, creams, absolutes, resins, resinoids, balms, tinctures such as Ambratincture; amyris oil; angelica seed oil; angelica root oil; anise oil; valerian oil; basil oil; tree moss absolute; bay oil; mugwort oil; benzoeresin; bergamot oil; beeswax absolute; birch tar oil; bitter almond oil; savory oil; bucco leaf oil; cabreuva oil; cade oil; calmus oil; Camphor oil; Cananga oil; Cardamom oil; Cascarilla oil; *Cassia* oil; Cassie absolute; Castoreum absolute; Cedar leaf oil; Cedar wood oil; Cistus oil; Citronella oil; Lemon oil; Copaiba balm; Copaiba balm oil; Coriander oil; Costus root oil; Cumin oil; Cypress oil; Davana oil; Dill weed oil; Dill seed oil; Eau de brouts absolute; Oak moss absolute; Elemi oil; Tarragon oil; Eucalyptus citriodora oil; Eucalyptus oil; Fennel oil; Spruce needle oil; Galbanum oil; Galbanumresin; Geranium oil; Grapefruit oil; Guaiac wood oil; Gurjun balm; Gurjun balm oil; Helichrysum absolute; Helichrysum oil; Ginger oil; Iris root absolute; Iris root oil; Jasmine absolute; Calmus oil; Camomile oil blue; Roman camomile oil; Carrot seed oil; Cascarilla oil; Pine needle oil; Curly mint oil; Caraway oil; Labdanum oil; Labdanum absolute; Labdanumresin; Lavandin absolute; Lavandin oil; Lavender absolute; Lavender oil; Lemongrass oil; Lovage oil; Distilled lime oil; Pressed lime oil; Linaloe oil; Litsea cubeba oil; Bay leaf oil; Macis oil; Marjoram oil; Mandarin oil; Massoirinden oil; Mimosa absolute; Musk seed oil; Musk tincture; Muscatel sage oil; Nutmeg oil myrrh absolute, myrrh oil; myrtle oil; clove leaf oil; clove flower oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil; Peppermint oil; Pepper oil; Allspice oil; Pine oil; Poley oil; Rose absolute; Rosewood oil; Rose oil; Rosemary oil; Sage oil Dalmatian; Sage oil Spanish; Sandalwood oil; Celery seed oil; Spiklavendel oil; Star anise oil; Styrax oil; Tagetes oil; Fir needle oil; Tea-tree oil; Turpentine oil; thyme oil; toluic balsam; tonka absolute; tuberose absolute; vanilla extract; violet leaf absolute; verbena oil; vetiver oil; juniper berry oil; wine yeast oil; wormwood oil; wintergreen oil; ylang oil; hyssop oil; civet absolute; cinnamon leaf oil; cinnamon bark oil; and fractions thereof, respectively or ingredients isolated therefrom;

Single Fragrance Substances from the Group of hydrocarbons, such as 3-carene; α-pinene; β-pinene; α-terpinene; γ-terpinene; p-cymene; bisabolene; camphene; caryophyllene; cedrene; farnesene; limonene; longifolene; myrcene; ocimene; valence; (E,Z)-1,3,5-undecatriene; styrene; diphenylmethane;

of aliphatic alcohols such as hexanol; octanol; 3-octanol; 2,6-dimethylheptanol; 2-methyl-2-heptanol; 2-methyl-2-octanol; (E)-2-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and their acetals such as hexanal; heptanal; octanal; nonanal; decanal; undecanal; dodecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethyl acetal; 1,1-dimethoxy-2,2,5-trimethyl-4-hexene; Citronellyloxy acetaldehyde; 1-(1-methoxy-propoxy)-(Z)-3-hexene; 1-(1-methoxy-propoxy)-(E)-3-hexene;

of aliphatic ketones and their oximes such as 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

of aliphatic sulfur-containing compounds such as 3-methylthiohexanol; 3-methylthiohexyl acetate; 3-mercaptohexanol; 3-mercaptohexyl acetate; 3-mercapto hexyl butyrate; 3-acetylthiohexyl acetate; 1-menthene-8-thiol;

aliphatic nitriles such as 2-nonononitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

the esters of aliphatic carboxylic acids such as (E)- and (Z)-3-hexenyl formate; ethyl acetoacetate; isoamyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerianate; ethyl 2-methyl pentanoate; ethyl hexanoate; allyl hexanoate; ethyl heptanoate; allyl heptanoate; ethyloctanoate; ethyl (E,Z)-2,4-decadienoate; methyl 2-octinate; methyl 2-noninate; allyl 2-isoamyloxy acetate; methyl 3,7-dimethyl-2,6-octadienoate; 4-methyl-2-pentyl crotonate;

the acyclic terpene alcohols such as Geraniol; Nerol; Lavadulol; Nerolidol; Farnesol; Tetrahydrolinalool; Tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; and their formates, acetates, propionates, isobutyrates, butyrates, isovalerianates, pentanoates, hexanoates, crotonates, tiglinates and 3-methyl-2-butenoates;

the acyclic terpene aldehydes and ketones such as citronellal; 7-methoxy-3,7-dimethyloctanal; 2,6,10-trimethyl-9-undecenal; geranyl acetone; and the dimethyl and diethyl acetals of geranial, neral, of cyclic terpene alcohols such as menthol; isopulegol; α-terpineol; terpinenol-4; menthan-8-ol; menthan-1-ol; menthan-7-ol; borneol; isoborneol; linalooloxide; nopol; cedrol; ambrinol; vetiverol; guaiol; as well as their formates, acetates, propionates, isobutyrates, butyrates, isovalerianates, pentanoates, hexanoates, crotonates, tiglinates and 3-methyl-2-butenoates;

the cyclic terpene aldehydes and ketones such as menthone; isomenthone; 8-mercaptomenthan-3-one; carvone; camphor; fenchone; α-ionone; β-ionone; α-n-methylionone; β-n-methylionone; α-isomethylionone; β-isomethyl-ionone; α-iron; β-damascenone; 1-(2,4,4-trimethyl-2-cyclohexen-1- yl)-2-buten-1-one; 1,3,4,6,7,8a-hexahydro-1,1,5,5-tetramethyl-2H-2,4a-methano-naphthalen-8(5H)-on; 2-methyl-4-(2,6,6-trimethyl-1-cyclohexen-1-yl)-2-butenal; nootkatone; dihydronootkatone; 4,6,8-megastigmatrien-3-one; α-sinensal; β-sinensal; acetylated cedar wood oil (methylcedrylketone);

of cyclic alcohols such as 4-tert-butylcyclohexanol; 3,3,5-tri methyl cyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as α-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-Methyl-5-(2,2,3-trimethyl-3-cyclopent-1-yl)-4-penten-2-ol; 3,3-Dimethyl-5-(2,2,3-trimethyl-3-cyclopent-1-yl)-4-penten-2-ol; 1-(2,2,6-Trimethylcyclohexyl)pentan-3-ol; 1-(2,2,6-Trimethylcyclohexyl)hexan-3-ol; of cyclic and cycloaliphatic ethers such as Cineol; cedrylmethylether; cyclododecylmethylether; 1,1-dimethoxycyclododecan; (ethoxymethoxy)cyclo-dodecan; α-Cedrenepoxid; 3a,6,6,9a-tetramethyldodecahydro-naphtho[2,1b] furan; 3a-Ethyl-6,6,9a-trimethyldodecahydronaphtho[2,1b]furan; 1,5,9-Trimethyl-13-oxabicyclo[10.1.0]trideca-4,8-dien; rose oxide; 2-(2,4-Dimethyl-3-cyclohexen-1-yl)-5-methyl-5-(1-methylpropyl)-1,3-dioxan;

the cyclic and macrocyclic ketones such as 4-tert-butylcyclohexanone; 2,2,5-trimethyl-5-pentylcyclopentanone; 2-heptylcyclopentanone; 2-pentyl-cyclo pentanone; 2-hydroxy-3-methyl-2-cyclopenten-1-one; 3-methyl-cis-2-penten-1-yl-2-cyclo penten-1-one; 3-methyl-2-pentyl-2-cyclopenten-1-one; 3-methyl-4-cyclopentadecenon; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexa decen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

of cycloaliphatic aldehydes such as 2-methyl-4-(2,2,6-trimethyl-cyclohexen-1-yl)-2-butenal; 4-(4-hydroxy-4-methyl-pentyl)-3-cyclohexencarbaldehyde; 4-(4-methyl-3-penten-1-yl)-3-cyclohexencarbaldehyde;

the cycloaliphatic ketones such as 1-(3,3-dimethylcyclohexyl)-4-penten-1-on; 2,2-dimethyl-1-(2,4-dimethyl-3-cyclohexen-1-yl)-1-propanon; 1-(5,5-dimethyl-1-cyclohexen-1-yl)-4-penten-1-on; 2,3,8,8-tetramethyl-1,2,3,4,5,6,7,8-octahydro-2-naphtalenylmethyl ketone; methyl-2,6,10-trimethyl-2,5,9-cyclododecatrienyl ketone; tert-butyl-(2,4-dimethyl-3-cyclohexen-1-yl)ketone;

the esters of cyclic alcohols such as 2-tert-butylcyclohexyl acetate; 4-tert-butylcyclohexyl acetate; 2-tert-pentylcyclohexyl acetate; 4-tert-pentyl-cyclohexyl acetate; 3,3,5-trimethylcyclohexyl acetate; decahydro-2-naphthyl acetate; 2-cyclo-pentylcyclo pentylcrotonate; 3-pentyltetrahydro-2H-pyran-4-yl acetate; decahydro-2,5,5,8a-tetramethyl-2-naphthyl acetate; 4,7-methano-3a,4,5,6,7,7a-hexa-hydro-5, respectively 6-indenyl acetate; 4,7-methano-3a,4,5,6,7,7a-hexahydro-5, or 6-indenyl propionate; 4,7-methano-3a,4,5,6,7,7a-hexahydro-5, or 6-inden-yl isobutyrate; 4,7-methanoocta hydro-5, or 6-indenyl acetate;

the esters of cycloaliphatic alcohols such as 1-cyclohexylethyl crotonate; the esters of cycloaliphatic carboxylic acids such as allyl 3-cyclohexyl propionate; allyl cyclohexyloxyacetate; cis- and trans-methyldihydrojasmonate; cis- and trans-methyljasmonate; methyl 2-hexyl-3-oxocyclopentanecarboxylate; ethyl 2-ethyl-6,6-dimethyl-2-cyclohexene carboxylate; ethyl 2,3,6,6-tetramethyl-2-cyclohexene carboxylate; ethyl 2-methyl-1,3-dioxolane-2-acetate;

the araliphatic alcohols such as benzyl alcohol; 1-phenylethyl alcohol; 3-phenyl propanol; 2-phenyl propanol; phenoxyethanol; 2,2-dimethyl-3-phenyl propanol; 2,2-dimethyl-3-(3-methylphenyl)propanol; 1,1-dimethyl-2-phenylethyl alcohol 1,1-di-methyl-3-phenylpropanol; 1-ethyl-1-methyl-3-phenylpropanol; 2-methyl-5-phenyl pentanol; 3-methyl-5-phenylpentanol; 3-phenyl-2-propen-1-ol; 4-methoxy benzyl alcohol; 1-(4-isopropylphenyl)ethanol;

the esters of araliphatic alcohols and aliphatic carboxylic acids such as benzyl acetate; benzyl propionate; benzyl isobutyrate; benzyl isovalerianate; 2-phenyl ethyl acetate; 2-phenylethyl propionate; 2-phenylethyl isobutyrate; 2-phenyl ethyl iso valerianate; 1-phenylethyl acetate; α-trichloromethyl benzyl acetate; α,α-dimethyl phenyl ethyl acetate; α,α-dimethyl phenyl ethyl butyrate; cinnamyl acetate; 2-phenoxyethyl isobutyrate; 4-methoxy benzyl acetate;

the araliphatic ethers such as 2-phenylethylmethylether; 2-phenylethyl-isoamylether; 2-phenylethyl-1-ethoxyethylether; phenylacetaldehyde dimethyl acetal; phenylacetaldehyde diethylacetal; hydratropic aldehyde dimethyl acetal; phenyl acetaldehyde glycerin acetal; 2,4,6-trimethyl-4-phenyl-1,3-dioxan; 4,4a,5,9b-tetra-hydroindeno[1,2-d]-m-dioxin; 4,4a,5,9b-tetrahydro-2,4-dimethylindeno[1,2-d]-m-dioxin;

the aromatic and araliphatic aldehydes such as benzaldehyde; phenylacetaldehyde; 3-phenylpropanal; hydratropic aldehyde; 4-methylbenzaldehyde; 4-methylphenylacetaldehyde; 3-(4-ethylphenyl)-2,2-dimethylpropanal; 2-methyl-3-(4-iso propyl phenyl)propanal; 2-methyl-3-(4-isobutylphenyl)propanal; 3-(4-tert-butyl-phenyl) propanal; cinnamic aldehyde; α-butyl cinnamaldehyde; alpha-hexyl cinnamaldehyde; 3-methyl-5-phenyl pentanal; 4-methoxybenzaldehyde; 4-hydroxy-3-methoxybenz-aldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as acetophenone; 4-methylacetophenone; 4-methoxyacetophenone; 4-tert-butyl-2,6-dimethylaceto-phenone; 4-phenyl-2-butanone; 4-(4-hydroxyphenyl)-2-butanone; 1-(2-naphtha-enyl)ethanone; 2-benzofuranylethanone; (3-methyl-2-benzofuranyl) ethanone; benzophenone; 1,1,2,3,3,6-hexamethyl-5-indanylmethylketone; 6-tert-butyl-1,1-di-methyl-4-indanylmethylketone; 1-[2,3-dihydro-1,1,2,6-tetramethyl-3-(1-methylethyl)-1H-5-indenyl]ethanone; 5',6',7',8'-tetra hydro-3',5',5',6',8',8'-hexamethyl-2-aceto-naphthone; the aromatic and araliphatic carboxylic acids and their esters such as benzoic acid; phenylacetic acid; methyl benzoate; ethyl benzoate; hexyl benzoate; benzyl benzoate; methyl phenyl acetate; ethyl phenyl acetate; geranyl phenyl acetate; phenyl ethyl phenyl acetate; methyl cinnamate; ethyl cinnamate; benzyl cinnamate; phenyl ethyl cinnamate cinnamyl cinnamate; allylphenoxy acetate; methyl salicylate; hexyl salicylate; cyclohexyl salicylate; cis-3-hexenyl salicylate; benzyl salicylate; phenyl ethyl salicylate; methyl 2,4-dihydroxy-3,6-dimethyl benzoate; ethyl 3-phenyl glycidate; ethyl 3-methyl-3-phenyl glycidate;

the nitrogenous aromatic compounds such as 2,4,6-trinitro-1,3-dimethyl-5-tert-butylbenzene; 3,5-dinitro-2,6-dimethyl-4-tert-butylacetophenone; cinnamic acid nitrile; 3-methyl-5-phenyl-2-pentenoic acid nitrile; 3-methyl-5-phenylpentanoic acid nitrile; methyl anthranilate; methyl N-methylanthranilate; Schiff bases of methyl anthranilate with 7-hydroxy-3,7-dimethyloctanal, 2-methyl-3-(4-tert-butyl-phenyl)propanal or 2,4-di methyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

of phenols, phenyl ethers and phenyl esters such as estragole; anethole; eugenyl methyl ether; isoeugenol; isoeugenyl methyl ether; thymol; carvacrol; diphenyl ether; 13 naphthyl methyl ether; β-naphthyl ethyl ether; β-naphthyl isobutyl ether; 1,4-dimethoxybenzene; eugenyl acetate; 2-methoxy-4-methylphenol; 2-ethoxy-5-(1-propenyl)phenol; p-cresylphenyl acetate;

of heterocyclic compounds such as 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one of lactones such as 1,4-octanolide; 3-methyl-1,4-octanolide; 1,4-nonanolide; 1,4-decanolide; 8-decene-1,4-olide; 1,4-undecanolide; 1,4-dodecanolide; 1,5-decanolide; 1,5-dodecanolide; 4-methyl-1,4-decanolide; 1,15-pentadecanolide; 1,16-hexadeca-nolide; 9-hexadecene-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; 2,3-dihydrocoumarin; octahydrocoumarin.

In a seventh aspect, the present invention relates to an olfactory and/or flavouring composition comprising
(a)-component: one or more compounds of formula (I), formula (Ia), formula (Ib), formula (Ic), formula (II) and/or formula (III) in variants according to the invention, and/or 2-(3-methylbutyl)cyclohexan-1-ol and/or 2-(3-methylbutyl) cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one, and
(b)-component: one or more, preferably two, three, four, five, six, seven, eight, nine, ten or more, other fragrances and/or flavours.

In a further variation, the present invention therefore concerns a fragrance and/or flavour composition comprising:
a) one or more compounds of the formula (I) according to claims 1 to 3 and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl) cyclohexan-1-ol, and/or 3-(3-methylbutyl)cyclohexan-1-one and (b) one or more, preferably two, three, four, five, six, seven, eight, nine, ten or more, other fragrance and/or flavour substances;
(i) the other fragrance and/or flavouring substance(s) imparting a woody, fruity and/or floral smell and/or taste, or
(ii) where the other fragrance and/or flavouring substance(s) impart a different odour.

In a preferred variant of an inventive odour and/or flavouring compositions, the inventive compounds or the inventive compounds to be used according to the invention of formula (I), formula (Ia), formula (Ib), formula (Ic), formula (II), and/or of formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl) cyclohexan-1-ol and/or 4-(3-methylbutyl)cyclohexan-1-one are preferably combined with one or more, especially preferably combined with two, three, four, five or more, floral and/or fruity further fragrances and/or aromas.

In a further preferred variant, the present invention relates to fragrance and/or flavouring compositions and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one, which comprises one, two, three, four, five or more fragrances and/or flavouring substances which impart a floral and/or fruity olfactory note.

In doing so, the inventive or inventively used compounds of formula (I), of formula (Ia), of formula (Ib), of formula (Ic), of formula (II) and/or of formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-on and/or 4-(3-methylbutyl)cyclohexan-1-ol and/or 4-(3-methylbutyl)cyclohexan-1-one advantageously (at least partially) achieve an olfactory enhancement of the floral odorants and/or flavorings.

Floral fragrances and/or aromatic substances with which the inventive or inventively used compounds of formula (I), of formula (Ia), of formula (Ib), of formula (Ic), of the formula (II) and/or of the formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl) cyclohexan-1-ol and/or 4-(3-methylbutyl)cyclohexan-1-one (in particular in fragrance and/or flavour compositions according to the invention) can be combined advantageously, are preferably selected from the group consisting of: Hydroxycitronellal, Methoxycitronellal, Cyclamenaldehyde [2-methyl-3-(4-isopropylphenyl)propanal], 1-(4-isopropyl-cyclohexyl)ethanol (Mugetanon, 4-tert-butyl-α-methyldihydrocinnamaldehyde (Lilian, cis-hexahydrocuminyl alcohol-(mayon, 3-[4-(1,1-dimethylethyl)phenyl]propanal (Bourgeonan, 2,2-dimethyl-3-(3-methyl phenyl) propanol (Majantol®), 3-methyl-3-(3-methylbenzyl)-butan-2-ol, 2-Isobutyl-4-methyl tetra hydro-2H-pyran-4-ol (Florosa®), 2-methyl-3-(3,4-methylenedioxyphenyl) propanal (Heliofolal®), 4-(4-hydroxy-4-methylpentyl)-3-cyclohexenecarbaldehyde (Lyral®), 4-(Octahydro-4,7-methano-5H-inden-5-ylidene butanal (Dupical®), vernaldehyde, 4-(4-methyl-3-penten-1-yl)-3-cyclohexene carbaldehyde (Vertomugal®), octahydro-5-(4-methoxybutylidene)-4,7-methano-1H-indene (Mugoflor®), 2,6-dimethyl-2-heptanol (Freesiol®), 1-ethyl-1-methyl-3-phenylpropanol (Phemec®), 2,2-dimethyl-3-phenyl-1-propanol (Muguet alcohol), profarnesol, dihydrofarnesol, farnesol, nerolidol, hydroxycitronellaldimethylacetal, hexylbenzoate, geraniol, nerol, linalool, tetrahydrogeraniol, tetrahydrolinalool, ethyllinalool, geranyltiglinate, phenethyl alcohol (2-phenylethyl alcohol), citronellol, Rose oxide, 2-methyl-5-phenylpentanol (rosaphene), 3-methyl-5-phenylpentanol (phenoxanol), methyl dihydrojasmonate (Hedion®, Hedione® high cis), 2-heptylcyclopentanone (Projasmon P), cis-jasmon, Dihydrojasmon, cinnamon alcohol (3-phenyl-2-propen-1-ol), dihydrocinnamon alcohol (3-phenylpropanol), 2-methyl-4-phenyl-1,3-dioxolane (Jacinthaflor®) and dihydromyrcenol (2,6-dimethyl-7-octen-2-ol).

In an eighth aspect, the present invention relates to a fragrance and/or flavouring composition, wherein the further one or more fragrance and/or flavouring substances are selected from the group consisting of ethyl 2-cyclopent-2-en-1-yl acetate, 1-cyclohexylethyl(E)-but-2-enoate, (2-cyclopentylcyclopentyl)(E)-but-2-enoate, allyl 3-cyclohexylpropanoate, allyl hexanoate, 1,3-dimethylbutyl (E)-but-2-enoate, 1,3-dimethylbut-3-enyl 2-methylpropanoate, and/or (E)-1-(2,6,6-trimethylcyclohex-2-en-1-yl)but-2-en-1-one.

In a preferred variant of an inventive odour and/or flavouring composition, the inventive or compounds of formula (I), formula (Ia), formula (Ib), formula (Ic) to be used according to the invention, of formula (II) and/or of formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one are preferably combined with one or more, particularly preferably combined with two, three, four, five or more further fragrances and/or flavouring substances, wherein the fragrances and/or flavouring substances are selected from the following group ethyl 2-cyclopent-2-en-1-yl acetate, 1-cyclohexylethyl (E)-but-2-enoate, (2-cyclopentylcyclopentyl) (E)-but-2-enoate, allyl 3-cyclohexylpropanoate, allyl hexanoate, 1,3-dimethyl butyl (E)-but-2-enoate, 1,3-dimethylbut-3-enyl 2-methylpropanoate, (E)-1-(2,6,6-trimethylcyclohex-2-en-1-yl)but-2-en-1-one.

In addition, inventive compounds or compounds which are to be used according to the invention of formula (I), of formula (Ia), of formula (Ib), of formula (Ic), of the formula (II) and/or of the formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one are advantageously suitable for intensifying the odour of, in particular, fruity odorous and/or flavour substances.

Fruity odoriferous and/or aromatic substances with which the inventive compounds or compounds which are to be used according to the invention, of formula (I), of formula (Ia), of formula (Ib), of formula (Ic), of the formula (II) and/or of the formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one, can be combined with advantageously, and which are therefore particularly preferred (further) odorants of an odorant and/or flavoring composition according to the invention, are preferably selected from the group consisting of: 2-methyl-butyric acid ethyl ester, 4-(p-hydroxyphenyl)-2-butanone, ethyl-3-methyl-3-phenylglycidate, isoamyl butyrate, isoamyl acetic acid ester, n-butyl acetic acid ester, ethyl butyrate, ethyl 3-methyl-butyrate, ethyl n-hexanoate, n-Hexanoic acid allyl ester, ethyl-2-trans-4-cis-decadienoate, 1,1-dimethoxy-2,2,5-trimethyl-4-hexane, 2,6-dimethyl-5-hepten-1-al, γ-undecalactone, γ-nonalactone, hexanal, 3Z-hexenal, n-decanal, n-dodecanal, citral, vanillin, ethylvanillin, maltol, ethylmaltol and mixtures thereof.

In a further variant, of the fragrance and/or flavouring composition, the weight ratio of the total amount of compounds of formula (I) or the aforementioned primary fragrance to the total amount of further fragrance and/or flavouring substances, preferably is in the range of 1:1000 to 1:0.5.

In a preferred inventive fragrance and/or flavoring mixture and/or—composition, the total amount of compounds of formula (I), formula (Ia), formula (Ib), formula (Ic) of formula (II) and/or of formula (III) and/or 2-(3-methylbutyl) cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one in the range of 0.0001 to 99.9 wt.-%, preferably in the range from 0.001 to 99.5% by weight, particularly preferably in the range from 0.01 to 99% by weight, in each case based on the total mass of the fragrance and/or flavoring mixtures and/or fragrance and/or flavoring compositions.

In further preferred inventive odorant and/or flavoring mixture and/or odorant—and/or flavoring composition, the total amount of compounds of the formula (I), the formula (Ia), the formula (Ib), the formula (Ic) of formula (II) and/or of formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one is in the range of 0.01 to 90 weight percent % by weight, preferably in the range from 0.05 to 80% by weight, more preferably in the range from 0.1 to 70% by weight, particularly preferably in the range from 0.25 to 50% by weight, particularly preferably in the range from 0.5 to 40% by weight, most preferably in the range from 0.75 to 25% by weight, in each case based on the total mass of the fragrance and/or flavour mixtures and/or fragrance—and/or flavour compositions.

In a preferred fragrance and/or flavouring substance mixture and/or fragrance and/or flavouring substance composition according to the invention, the total amount used of the compound(s) of formula (I), formula (Ia), formula (Ib), formula (Ic), formula (II) and/or formula (III) in variants according to the invention is sufficient, in order to modify or to enhance the smell of the other fragrances and/or flavours in the direction of green, herbaceous, fresh, fruity, floral, woody, sweet, earthy, greasy, metallic and balsamic, preferably in the direction of green and/or fruity, preferably in the direction of rose, and/or to convey one or more of the said notes.

If one or more compounds of formula (I), formula (Ia), formula (Ib), formula (Ic), of formula (II) and/or of formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one is mainly used to impart more freshness, (radiance), rounding off, harmony and/or naturalness to a fragrance and/or flavouring mixture and/or fragrance and/or flavouring compositions and/or to enhance certain notes (already present through other fragrances or flavouring substances), the total amount of component (a) is preferably comparatively low and particularly preferably in the range of 0.01 to 5 wt.-%.%, preferably in the range of 0.1 to 2% by weight, based on the total amount of the fragrance and/or flavour mixtures and/or fragrance—and/or flavour compositions. If a comparatively low concentration is selected within the preferred concentration ranges, the above-mentioned inherent odour notes are not yet conveyed in some cases, depending on the other components of the respective composition.

The preferential embodiments of the invention described above with a view to the uses according to the invention shall apply mutatis mutandis also to inventive odour and/or flavouring mixtures and/or odour and/or flavouring compositions as well as perfumed articles according to the invention, in particular the information on preferred weight ratios.

The compound(s) of the formula (I), the formula (Ia), the formula (Ib), the formula (Ic) and/or the formula (II) according to the invention or to be used according to the invention, in particular the compounds of the formula (I), the formula (Ia), the formula (Ib), the formula (Ic), the formula (II) and/or the formula (III) which are designated as preferred or particularly preferred in the context of this invention have a very complex and varied olfactory impression. Otherwise, this impression can usually only be achieved by mixing several components (such as essential oils or spice mixtures).

In addition to their primary, i.e. odoriferous, properties, the compounds of formula (I), formula (Ia), formula (Ib), formula (Ic), formula (II) and/or formula (III) also have positive secondary properties, in particular good adhesion and high substantivity in comparison with odoriferous and/or aromatic substances with similar odoriferous properties, as well as high stability in certain media and preparations and high yield.

In an eighth aspect, the invention relates to a process for modifying and/or enhancing (boosting) an odour with one, several or all of the notes fruity and/or woody and comprises the following steps:
(a) Providing a compound of formula (I), formula (Ia), formula (Ib), formula (Ic), formula (II) and/or formula (III) according to any of the foregoing claims 1 to 3 and/or a fragrance mixture(s) and/or—composition(s) according to the invention;
(b) Blending a sensory effective amount of this substance or substances with a mixture of one or more olfactory and/or aromatic substance(s) with one or more of the notes fruity and/or woody,
which is sufficient to evoke, sensory modify and/or enhance a fruity and/or woody odor in the finished preparation.

The inventive or compounds of formula (I), formula (Ia), formula (Ib), formula (Ic) to be used according to the invention, of formula (II) and/or of formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one can also enhance the intensity of a fragrance and/or flavor mixture according to the invention and round off the overall olfactory appearance of the mixture and can be used to give a fragrance and/or flavor composition more fullness, freshness, (radiance) power, radiance, luster, rounding off, harmony and/or naturalness.

One or more compounds of formula (I), of formula (Ia), of formula (Ib), of formula (Ic), of formula (II) and/or of formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one and/or 3-(3-methylbutyl)cyclohexan-1-ol, and/or 3-(3-methylbutyl)cyclohexan-1-one can be used in particular to impart freshness, (radiance), rounding off, harmony and/or naturalness to an odorant and/or flavoring composition and/or to intensify existing odor notes.

In a ninth aspect, the present invention concerns the use of one or more compounds of formula (I), formula (Ia), formula (Ib), formula (Ic), of formula (II) and/or of formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-meth-ylbutyl)cyclohexan-1-one and/or 3-(3-methylbutyl)cyclohexan-1-ol, and/or 3-(3-methylbutyl)cyclohexan-1-one for imparting a fragrance to hair and/or skin or textile fibers (for the preferred olfactory notes, please refer to the above explanations), wherein the compound(s) of formula (I), of formula (Ia), of formula (Ib), of formula (Ic), of formula (II) and/or of formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one is preferably used in combination with a surfactant or a surfactant mixture or are used.

In a ninth aspect, the present invention concerns the use of the compounds of formula (I), formula (Ia), formula (Ib), formula (Ic), of formula (II) and/or of formula (III) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one fragrance and/or flavouring mixtures and/or fragrance—and/or flavouring compositions as means for increasing the substantivity and/or retention of a fragrance and/or flavouring mixture and/or fragrance and/or flavouring composition and/or as a fixator.

The sensory properties of compounds of formula (I) and their suitability as fragrance and/or flavoring agents have not yet been described and show surprising advantages, in particular increased substantivity.

The following Table 1 contains the sensory, in particular the olfactory, descriptions of some compounds of formula (I) which are, or are to be used, according to the invention.

Decisive is always the shown structural formula of the compounds of formulas (I).

TABLE 1

| No.: | Structure | Sensory Description | substantivity |
|---|---|---|---|
| 11 | OH | rosy, greasy, green | good adhesion $t\ 1/2 = 3d$ after 48 h still smelling |
| 12 | OH | rosy, green | good adhesion $t\ 1/2 = 3d$ after 48 h still smelling |
| 5 | O | rosy, aldehydic, floral, green, citronellol | very good adhesion $t\ 1/2 = 3d$ still smelling strongly after 48 h |

TABLE 1-continued

| No.: | Structure | Sensory Description | substantivity |
|---|---|---|---|
| 6 | [cyclohexane with CH2OH and 3-methylbutyl substituents] | strongly rosy, natural | very good adhesion t 1/2 = 3d still smelling strongly after 48 h |
| 7 | [cyclohexane with CHO and 3-methylbutyl substituents] | aldehydic, floral, green | very good adhesion t 1/2 = 3d still smelling strongly after 48 h |
| 8 | [cyclohexane with CH2OH and 3-methylbutyl substituents] | Graph fruit, rosy, fruity | very good adhesion t 1/2 = 3d still smelling strongly after 48 h |
| 9 | [cyclohexane with CHO and 3-methylbutyl substituents] | leathery, marine, graph fruit, rhubarb ozone-like, floral, green | very good adhesion t 1/2 = 3d still smelling strongly after 48 h |
| 10 | [cyclohexane with CH2OH and 3-methylbutyl substituents] | flowery, rosy, grassy | very good adhesion t 1/2 = 3d, dry down after 48 h still smelling strongly |

Fragrance combinations or fragrance compositions are still particularly preferred. Here, an extraordinary increase in the fruity note of some fragrances was achieved by combining them with other second fragrances. The following Table 2 contains the sensory, especially the olfactory, descriptions of 4-(3-methylbutyl)cyclohexan-1-ol (Symrose) with secondary or combined fragrances.

TABLE 2

| No.: | Second fragrance name | Structure | Dosage from Symrose with secondary fragrance | Odor mixed |
|---|---|---|---|---|
| 21 | Sultanene | [cyclopentenyl ethyl acetate structure] | 0.5-1% | softer, rounder, fruitier, less metallic |
| 22 | Aprifloren | [methyl hexyl lactone structure] | 0.5-1% | Reduction of unpleasant greasy notes |
| 23 | Datilat | [cyclohexyl ethyl crotonate structure] | 0.5-1% | more impact, more dry and fruity towards plum |
| 24 | Buccoxime | [bicyclic oxime structure] | 0.5-1% | softer, rounder, less technical |

TABLE 2-continued

| No.: | Second fragrance name | Structure | Dosage from Symrose with secondary fragrance | Odor mixed |
|---|---|---|---|---|
| 25 | Vertacetal Coeur | 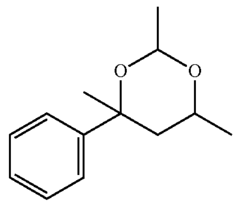 | 0.5-1% | less unpleasantly musty, more natural |
| 26 | Oxanthia 50% in TEC | 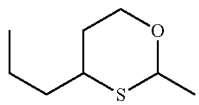 | 0.5-1% | softer, rounder, fruitier, less metallic |
| 27 | Cassiffix | 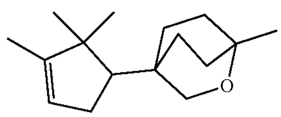 | 0.5-1% | more fruity, round and natural |
| 28 | Amarocit | 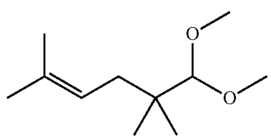 | 0.5-1% | more fruity and greener, more natural |
| 29 | Isoamyl acetate | 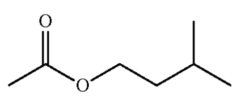 | 0.5-1% | softer, rounder, more natural, less metallic |
| 30 | Fragolans | 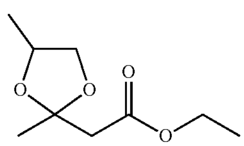 | 0.5-1% | softer, rounder, less metallic |
| 31 | Ethyl methyl butyrate-2 | 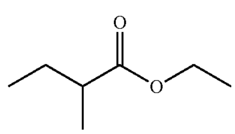 | 0.5-1% | fruity, round |
| 32 | Pyroprunate | 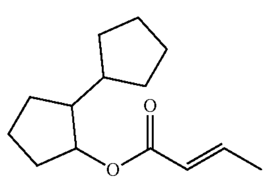 [SMILES: C/C=C/C(=O)OC1CCCC1C1CCCC1] | 0.5-1% | fruity-sweeter, more ripe fruit |
| 33 | Cassix 150 | 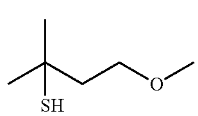 | 0.5-1% | more fruity, round and natural |
| 34 | Allylcyclohexylpropionate | 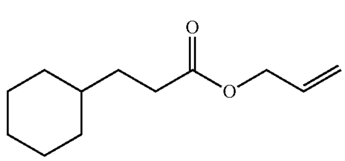 | 0.5-1% | stronger fruity |

TABLE 2-continued

| No.: | Second fragrance name | Structure | Dosage from Symrose with secondary fragrance | Odor mixed |
|---|---|---|---|---|
| 35 | Allyl Capronate | 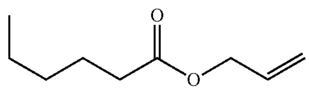 | 0.5-1% | stronger fruity |
| 36 | Frutinate | 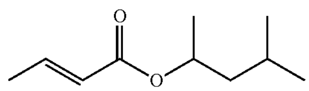 | 0.5-1% | more impact, juicier-fruity, more natural |
| 37 | Isopentyrate | 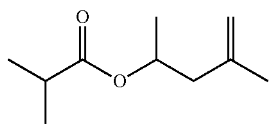 | 0.5-1% | more impact, more radiation, more natural, sweeter |
| 38 | Damascone alpha | 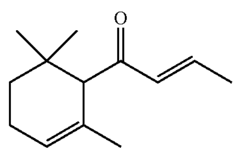 | 0.5-1% | softer, rounder, fruitier, less metallic |

In a preferred variant, the invention relates to fragrance compositions and fragrance combinations, comprehensive: one or more compounds of formula (I) according to variants according to the invention and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol- and/or 4-(3-methylbutyl)cyclohexan-1-one and/or 3-(3-methylbutyl)cyclohexan-1-ol, and/or 3-(3-methylbutyl)cyclohexan-1-one and at least one fragrance and/or flavoring mixture in a sensory effective amount, the fragrance and/or flavoring mixture(s) being selected from the following group: ethyl 2-cyclopent-2-en-1-yl acetate, 1-cyclohexylethyl (E)-but-2-enoate, (2-cyclo pentylcyclopentyl) (E)-but-2-enoate, allyl 3-cyclohexylpropanoate, allyl hexanoate, 1,3-dimethylbutyl (E)-but-2-enoate, 1,3-dimethylbut-3-enyl 2-methyl propanoate, and/or (E)-1-(2,6,6-trimethylcyclohex-2-en-1-yl)but-2-en-1-one.

By combining 4-(3-methylbutyl)cyclohexan-1-ol (Symrose) with other second fragrances, the olfactory impression of the fragrances is enhanced. They often appear more fruity and natural and therefore take on a slightly modified character. False odours such as metallic notes are no longer perceived.

Preferably, Symrose or other compounds mentioned in the invention are combined with the following second fragrances: Sultanene, Aprifloren, Datilat, Buccoxime, Vertacetal Coeur, Oxanthia 50% in TEC, Cassiffix, Amarocit, Fragolane, Pyroprunate, Cassix 150, Allylcyclohexylpropionate, Allylcapronate, Frutinate, Isopentyrate, Damascone alpha.

The following variants and basic fragrances of the compounds 3-(3-methylbutyl)cyclohexan-1-one (2) or 3-(3-methylbutyl)cyclohexan-1-ol (3) also give an enhanced synergistic fruity odor with the second or combination fragrances listed in Table 2.

In a tenth aspect, the invention concerns perfumed or flavoured articles, comprising:

i) one or more compounds of formula (I) according to variants of the invention and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one and/or a fragrance and/or flavoring mixture and/or—composition in a sensory effective amount, ii) one, two, three, four, five, six, seven, eight, nine, ten or more other odoriferous or aromatic substances, preferably one, several or all of the other odoriferous substances conveying a fruity and/or woody odor, iii) one or more further additives, excipients and/or active substances, preferably two, three, four, five or more additives, excipients and/or active substances. It goes without saying that the other additives, auxiliaries and/or active ingredients are not fragrances or flavors.

In a preferred embodiment, the invention relates to perfumed or flavoured articles, comprehensive: one or more compounds of formula (I) according to variants according to the invention and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one and at least one fragrance and/or flavoring mixture in a sensory effective amount, the fragrance and/or flavoring mixture(s) being selected from the following group: ethyl 2-cyclopent-2-en-1-yl acetate, 1-cyclohexylethyl (E)-but-2-enoate, (2-cyclopentylcyclopentyl) (E)-but-2-enoate, allyl 3-cyclohexylpropanoate, allyl hexanoate, 1,3-dimethylbutyl (E)-but-2-enoate, 1,3-dimethylbut-3-enyl 2-methyl propanoate, and/or (E)-1-(2,6,6-trimethylcyclohex-2-en-1-yl) but-2-en-1-one.

Additives, adjuvants and/or active ingredients, which are a perfumed or aromatized article according to the invention, in addition to one or more compounds of formula (I), of formula (Ia), of formula (Ib), of formula (Ic), and/or of formula (II) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one and/or a fragrance and/or flavouring mixture and/or fragrance and/or flavouring composition (as defined below) according to the invention are preferably selected from the group consisting of:

Preservatives, preferably those mentioned in US 2006/0089413, abrasives, anti-acne agents and agents for sebum reduction, preferably those mentioned in WO 2008/046791, agents against skin aging, preferably those mentioned in WO 2005/123101, antibacterial agents, anti-cellulitis agents, anti-dandruff agents, preferably the anti-inflammatory agents, irritation inhibiting agents, anti-irritants (anti-inflammatory, irritation inhibiting and irritation preventing agents) mentioned in WO 2008/046795, preferably those mentioned in WO 2007/042472 and US 2006/0089413, antimicrobial agents, preferably those mentioned in WO 2005/123101, antioxidants, preferably those mentioned in WO 2005/123101, astringents, antiseptic agents, antistatic agents, binders, buffers, carrier materials, preferably those mentioned in WO 2005/123101, chelating agents, preferably those mentioned in WO 2005/123101, cell stimulants, cleansing agents, skin care products, depilatories, surface-active substances, deodorants and antiperspirants, preferably those mentioned in WO 2005/123101, plasticizers, emulsifiers, preferably those mentioned in WO 2005/123101, enzymes, essential oils, preferably those mentioned in US 2008/0070825, insect repellents, preferably those mentioned in WO 2005/123101, fibers, film formers, (further) fixatives, foaming agents, foam stabilizers, anti-foaming substances, foam boosters, fungicides, gelling and gel-forming agents, preferably those mentioned in WO 2005/123101, hair care products, hair shaping agents, hair straightening agents, moisture regulators (moisturizing and conditioning agents), preferably those mentioned in WO 2005/123101, osmolytes, preferably the osmolytes mentioned in WO 2005/123101, compatible solutes, preferably the compatible solutes mentioned in WO 01/76572 and WO 02/15686, bleaching agents, strengthening agents, stain-removing agents, optical brightening agents, impregnating agents, stain-repellent agents, friction-reducing agents, lubricants, moisturizers, ointments, opacifiers, plasticizers, covering agents, polish, glazing agents, polymers, preferably mentioned in WO 2008/046676, powders, proteins and protein hydrolysates, preferably mentioned in WO 2005/123101 and WO 2008/046676, refatting agents, abrasives, skin calming agents, skin cleansing agents, skin care agents, skin repair agents, preferably containing cholesterol and/or fatty acids and/or ceramides and/or pseudoceramides, preferably mentioned in WO 2006/053912, skin lightening agents, preferably mentioned in WO 2007/110415, skin protecting agents, skin softening agents, skin cooling agents, preferably those mentioned in WO 2005/123101, skin-warming agents, preferably those mentioned in WO 2005/123101, stabilizers, UV absorbing agents and UV filters, preferably those mentioned in WO 2005/123101 Benzylidene-β-dicarbonyl compounds, preferably those mentioned in WO 2005/107692, α-benzoyl cinnamic acid nitriles, preferably those mentioned in WO 2006/015954, AhR receptor antagonists, preferably those mentioned in WO 2007/128723 and WO 2007/060256, detergents, fabric softeners, suspending agents, skin tanning agents, preferably those mentioned in WO 2006/045760, thickening agents, vitamins, preferably those mentioned in WO 2005/123101, fatty oils, waxes and fats, preferably those mentioned in WO 2005/123101, phospholipids, preferably those mentioned in WO 2005/123101 Fatty acids (saturated fatty acids, mono- or polyunsaturated fatty acids, α-hydroxy acids, polyhydroxy fatty acids), preferably those mentioned in WO 2005/123101, dyes and color-protecting agents as well as pigments, preferably those mentioned in WO 2005/123101, anti-corrosives, alcohols and polyols, preferably those mentioned in WO 2005/123101, surfactants, preferably those mentioned in WO 2005/123101, animal extracts, yeast extracts, extracts of algae or microalgae, electrolytes, liquefiers, organic solvents, preferably the hair growth modulating agents mentioned in WO 2005/123101 (hair growth promoting or hair-growth inhibiting), preferably those mentioned in EP 2168570 and EP 2193785 or silicones and silicone derivatives, preferably those mentioned in WO 2008/046676.

A preferred embodiment of the present invention relates to perfumed or flavoured articles comprising
  one or more compounds of formula (I), of formula (Ia), of formula (Ib), of formula (Ic), and/or of formula (II) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one and/or a fragrance and/or flavouring mixture and/or fragrance and/or flavouring composition, preferably in one of the forms indicated above as preferred, in a sensory effective amount which is sufficient to impart, modify and/or enhance, preferably impart and/or enhance one or more of the odour notes green, herbaceous, fresh, fruity, floral, woody, sweet, earthy, fatty, metallic and balsamic,
  one, two, three, four, five, six, seven, eight, nine, ten or more further perfuming and/or flavouring substances, preferably one, two, three or more of the further perfuming and/or flavouring substances imparting a woody, fruity and/or floral odour,
  two, three, four, five or more additives, auxiliaries and/or active ingredients, preferably one, two, three or more additives, auxiliaries and/or active ingredients being selected from the group consisting of preservatives, inorganic salts, chelating agents, surfactants, skin and/or hair care agents, enzymes, emulsifiers, fats, fatty oils, waxes, fatty alcohols, silicones, silicone-derivatives and water.

A further preferred embodiment of the present invention relates to articles which, according to the invention, are perfumed or flavoured, selected from the group consisting of washing and cleaning agents, hygiene or care products, in particular in the field of personal and hair care, cosmetics and household goods.

Since a fragrance and/or flavoring composition according to the invention is suitable for perfuming or aromatizing articles, the invention relates in a further preferred embodiment to a perfumed or aromatized article, comprising
  a fragrance composition according to the invention, preferably in one of the forms designated as preferred, preferably in a sensory effective amount, and
  one or more further additives, adjuvants and/or active substances, preferably two, three, four, five or more additives, adjuvants and/or active substances, preferably two, three, four, five or more of the additives, adjuvants and/or active substances indicated above as preferred.

An alternative inventively preferred variation of the present invention relates to perfumed or flavoured articles, which are selected from the group consisting of perfume extracts, eau de parfums, eau de toilettes, aftershave lotions, eau de colognes, pre-shave products, splash colognes, perfumed refreshing tissues, acidic, alkaline or neutral detergents, textile fresheners, ironing aids, liquid detergents, powdered detergents, laundry pre-treatment agents, fabric softeners, washing soaps, washing tablets, disinfectants, Surface disinfectants, air fresheners, aerosol sprays, waxes and polishes, personal care products, hand creams and lotions, foot creams and lotions, depilatory creams and lotions, after-shave creams and lotions, tanning creams and lotions, hair care products, deodorants, antiperspirants, decorative cosmetic products, candles, lamp oils, incense sticks, insecticides, repellents and fuels.

Another preferred variation of the present invention concerns perfumed or flavoured articles in which the total amount of compounds of formula (I), formula (Ia), formula (Ib), formula (Ic), and/or of formula (II) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one and/or a fragrance and/or flavouring mixture and/or fragrance- and/or flavouring compositions according to the invention, preferably in one of the forms indicated above as preferred, in the range from 0.00001 to 10 wt.-%, preferably in the range from 0.0001 to 5% by weight, more preferably in the range from 0.001 to 2% by weight, most preferably from 0.005 to 1% by weight, each based on the total mass of the perfumed or flavored article.

The invention relates in an eleventh aspect to the use of an inventive odorant and/or flavoring composition, preferably in one of the forms indicated as preferred,
(A) as fragrance and/or flavour composition
  (a) (i) with a rose note, and/or
    (ii) for imparting, modifying and/or enhancing one or more olfactory notes selected from the group consisting of the notes green, herbaceous, fresh, fruity, floral, woody, sweet, earthy, fatty, metallic and balsamic, preferably at least one of the notes green and/or fruity, and/or
  (b) (i) with a fruity and/or floral note, and/or
    (ii) for imparting, modifying and/or enhancing one or more olfactory and/or gustatory notes selected from the group consisting of woody, fruity and/or floral notes, and/or
  (c) with floral, fruity, rose note
and/or
(B) as a component of a perfumed or flavoured article.

Perfuming and/or flavouring compositions according to the invention, comprising one or more compounds of the formula (I), of the formula (Ia), of the formula (Ib), of the formula (Ic), and/or of formula (II) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one can be used in liquid form, undiluted or diluted with a solvent for perfuming. Preferred solvents are ethanol, isopropanol, diethylene glycol monoethyl ester, glycerol, propylene glycol, 1,2-butylene glycol, dipropylene glycol, diethyl phthalate, triethyl citrate, isopropyl myristate, triacetin and diacetin.

Furthermore, perfuming and/or flavouring compositions according to the invention, which contain compounds of the formula (I), of the formula (Ia), of the formula (Ib), of the formula (Ic), and/or of formula (II) and/or 2-(3-methylbutyl)cyclohexan-1-ol and/or 2-(3-methylbutyl)cyclohexan-1-one and/or 3-(3-methylbutylcyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one may be adsorbed on a carrier which ensures both a fine distribution of the fragrances and/or flavours in the product and a controlled release during use. Such carriers can be porous inorganic materials such as light sulfate, silica gels, zeolites, gypsum, clays, clay granules, aerated concrete, etc. or organic materials such as wood, cellulose-based materials, sugar, dextrins (e.g. maltodextrin) or plastics such as PVC, polyvinyl acetates or polyurethanes. The combination of inventive composition and carrier material represents an exemplary inventive article.

Fragrance and/or flavor compositions containing compounds according to the invention can also be microencapsulated, spray-dried, as inclusion complexes or as extrusion products (i.e. articles according to the invention) and added in this form, e.g. to a product to be perfumed.

If necessary, the properties of the compositions modified in this way can be further optimized by so-called "coating" them with suitable materials with a view to more targeted fragrance release, preferably using wax-like plastics such as polyvinyl alcohol. The resulting products in turn represent articles that are in accordance with the invention.

The microencapsulation of the olfactory and/or aromatic substance compositions according to the invention into articles according to the invention can be achieved, for example, by the so-called coacervation process using capsule materials, e.g. made of polyurethane-like substances or soft gelatine. The spray-dried fragrance and/or flavour compositions can be produced, for example, by spray-drying an emulsion or dispersion containing the fragrance and/or flavour composition, whereby modified starches, proteins, dextrin and vegetable gums can be used as carriers. Inclusion complexes can be prepared e.g. by adding dispersions of the fragrance and/or flavour composition and cyclodextrins or urea derivatives in a suitable solvent, e.g. water. Extruded products can be obtained by fusing the fragrance and/or flavoring compositions with a suitable waxy substance and by extrusion with subsequent solidification, if necessary in a suitable solvent, e.g. isopropanol.

Compounds of formula (I), formula (Ia), formula (Ib), formula (Ic), and/or formula (II) and fragrance compositions according to the invention, which comprises one or more compounds of the formula (I) and/or 2-(3-methylbutyl)cyclohexan-1-ol and/or 2-(3-methylbutyl)cyclohexan-1-one and/or 3-(3-methylbutyl)cyclohexan-1-ol and/or 3-(3-methylbutyl)cyclohexan-1-one and/or 4-(3-methylbutyl)cyclohexan-1-ol and/or 4-(3-methylbutyl)cyclohexan-1-one and/or 3-(3-methylbutyl)cyclohexan-1-ol, and/or 3-(3-methylbutyl)cyclohexan-1-one may be used in concentrated form, in solutions or in the modified form described above for the manufacture of perfumed or flavoured articles of the invention, such as perfume extracts, eau de parfums, eau de toilettes, aftershave lotions, eau de colognes, pre-shave products, splash colognes and perfumed refreshing tissues as well as the perfuming of acidic, alkaline and neutral detergents, such as floor cleaners, window glass cleaners, dishwashing detergents, bath and sanitary cleaners, scouring milk, solid and liquid toilet cleaners, powder and foam carpet cleaners, textile fresheners, ironing aids, liquid detergents, powder detergents, laundry pre-treatment agents such as bleach, soaking agents and stain removers, washing softeners, washing soaps, washing tablets, disinfectants, surface disinfectants and air fresheners in liquid, gel or solid form, aerosol sprays, waxes and polishes such as furniture polishes, floor waxes, shoe polishes and body care products such as e.g. solid and liquid soaps, shower gels, shampoos, shaving soaps, shaving foams, bath oils, oil-in-water, water-in-oil and water-in-oil-in-water cosmetic emulsions such as skin creams and lotions, face creams and lotions, sun protection creams and lotions, after-sun creams and lotions, hand creams and lotions, foot creams and lotions, depilatory creams and lotions, after-shave creams and lotions, tanning creams and lotions, hair care products such as e.g. hair sprays, hair gels, firming hair lotions, hair conditioners, permanent and semi-permanent hair dyes, hair shaping agents such as cold wave and hair-straightening agents, hair lotions, hair creams and lotions, deodorants and antiperspirants such as e.g. underarm sprays, roll-ons, deodorant sticks, deodorant creams, products of decorative cosmetics such as eye shadow, nail polishes, make-up, lipsticks, mascara as well as candles, lamp oils, incense sticks, insecticides, repellents and fuels.

The spray-dried solid preparations according to the invention (as an example of an article corresponding to the invention) are, as semi-finished goods, particularly suitable for the manufacture of further preparations according to the invention. The spray-dried solid preparations according to the invention preferably contain 50 to 95% by weight of excipients, in particular maltodextrin and/or starch, 5 to 40% by weight of auxiliary substances, preferably natural or artificial polysaccharides and/or plant gums such as modified starches or gum arabic.

The invention relates in a twelfth aspect to a process for imparting, modifying and/or enhancing one or more olfactory notes selected from the group consisting of the notes green, herbaceous, fresh, fruity, floral, woody, sweet, earthy, greasy, metallic and balsamic, preferably at least one of the notes green and/or fruity, preferably a rose note, comprising the following steps:
  providing one or more compounds of formula (I) as defined above, preferably in one of the forms indicated above as preferred, or an olfactory and/or flavouring composition as defined above, preferably in one of the forms indicated above as preferred,
  provision of an article,
  bringing the article into contact with a sensory effective amount of the compound(s) of formula (I) or of the fragrance and/or flavouring composition as defined above.

A corresponding preferred method according to the invention is a method in which, after contact, (i) a perfumed or aromatized article results or (ii) is produced from the then present article selected from the group consisting of:
perfume extracts, eau de parfums, eau de toilettes, shaving lotions, eau de colognes, pre-shave products, splash colognes, perfumed refreshing tissues, acid, alkaline or neutral detergents, textile fresheners, ironing aids, liquid detergents, powder detergents, laundry pre-treatment products, fabric softeners, washing soaps, washing tablets, disinfectants, surface disinfectants, Air fresheners, aerosol sprays, waxes and polishes, personal care products, hand creams and lotions, foot creams and lotions, depilatory creams and lotions, after-shave creams and lotions, tanning creams and lotions, hair care products, deodorants, antiperspirants, decorative cosmetic products, candles, lamp oils, incense sticks, insecticides, repellents and fuels.

The invention relates in a thirteenth aspect to a process for the preparation of a compound of formula (I), formula (Ia), formula (Ib), formula (Ic) and/or formula (II) according to the invention or to be used according to the invention. The synthesis can be carried out by means of reactions and processes known per se. For example, the ketone (2) can be prepared by a 1,4-Grignard reaction from the compound 2-cyclohex-3-en (compound 1). The subsequent reduction of the ketone (2) results in the alcohol (3) (see scheme 1 below).

Scheme 1

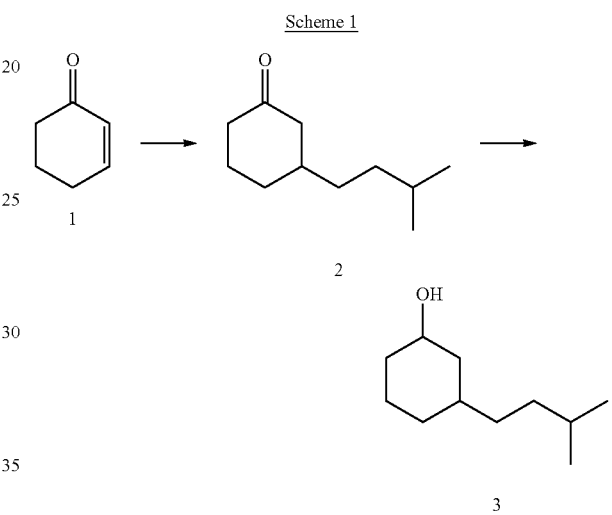

The invention relates in a fourteenth aspect to a process for the preparation of a compound (I) comprising at least steps (i), (ii) and (iii), characterized in that starting from 2-, or 3-, or 4-isopentlyclohexanone by i) Wittig reaction 1-isopentyl-2-(methoxymethylene)cyclohexane (compound 4a), 1-isopentyl-3-(methoxymethylene)cyclohexane (compound 4b), or 1-isopentyl-4-(methoxymethylene)cyclohexane (compound 4c) is obtained, ii) subsequent enol splitting leads to aldehyde (compound 5 a, b, c)

iii) and by optionally subsequent reduction of the alcohol (compound 6 a, b, c) (see Scheme 2 below).

Scheme 2

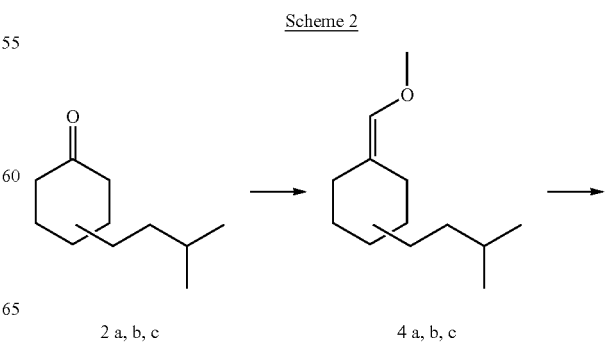

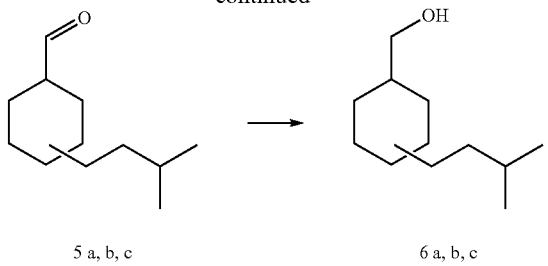

5 a, b, c → 6 a, b, c

In the following, the invention is explained in more detail using examples. Unless otherwise indicated, all data refer to weight.

When specifying decimal places, a dot was used instead of a comma, contrary to German spelling.

Abbreviations used: DPG: dipropylene glycol, TEC: triethyl citrate, MTBE: methyl tert-butyl ether, THF: tetrahydrofuran, LAH: lithium aluminium hydride, RT: room temperature.

DETAILED DESCRIPTION OF THE INVENTION

The invention is described below by means of embodiments. As will be explained in more detail below, the compounds of formula (I) according to the invention can be synthesized in the following manner described below. Furthermore, it should be noted that the IUPAC nomenclature may differ from the previously used generic terms.

Example 1: 3-isopentylcyclohexanone (2)

Preparation of the Grignard reagent: Lightly grind magnesium shavings (16.5 g, 0.687 mol) in a mortar and place in a flask in 300 ml THF, add a spatula tip of iodine, heat under reflux (solution must decolorize) only then 1/10 of 3-methylbutyl bromide (93.8 g, 0.621 mol), after the Grignard reagent has started to form, drop the remaining 3-methylbutylbromide into 150 ml THF, reflux the preparation for 1 hour, and then allow the preparation to cool.

The Grignard solution is transferred via a cannula into a well stirred suspension of copper iodide (8.0 g, 0.042 mol) cooled to −5° C. in 300 ml THF. After dissolving the copper iodide, allow to cool to −20° C. and drop cyclohex-2-en-1-one (34 g, 0.354 mol) and stir at −20° C. for 4 hours (h), then thaw to RT and stir overnight. Preparation: Place the preparation in 600 ml ice-cold saturated ammonium chloride solution, add 300 ml MTBE. Phase separation; extract three times with 100 ml MTBE and wash, dry and concentrate the combined organic phases twice with 200 ml saturated (total) NaCl solution. The raw product (60.0 g) was fractionally distilled on a 15 cm Vigreux column under vacuum.

Yield: 52.0 g (87%)

$^1$H-NMR (400 MHz, CDCl$_3$) δ 2.42 (ddt, J=13.8, 4.0, 1.9 Hz, 1H), 2.35 (dddt, J=14.1, 5.0, 3.6, 1.5 Hz, 1H), 2.25 (dddd, J=14.1, 12.2, 6.1, 1.2 Hz, 1H), 2.04 (dddd, J=13.8, 8.0, 6.3, 3.9 Hz, 1H), 2.00 (ddt, J=13.7, 11.6, 1.1 Hz, 1H), 1.96-1.84 (m, 1H), 1.79-1.70 (m, 1H), 1.70-1.58 (m, 1H), 1.50 (dp, J=13.2, 6.6 Hz, 1H), 1.40-1.24 (m, 3H), 1.23-1.14 (m, 2H), 0.87 (d, J=6.6 Hz, 6H);

$^{13}$C-NMR (101 MHz, CDCl$_3$) δ 212.16 (C=O), 48.31 (CH$_{2\text{-}ring}$), 41.55 (CH$_{2\text{-}ring}$), 39.38 (CH-ring), 35.91 (CH$_2$), 34.35 (CH$_2$), 31.35 (CH$_{2\text{-}ring}$), 28.08 (CH—(CH$_3$)$_2$, 25.32 (CH$_{2\text{-}ring}$), 22.58 (CH—(CH3)$_2$, 22.57 (CH—(CH3)$_2$.

Example 2: 3-isopentylcyclohexanol (3)

LAH (2.48 g, 0.065 mol) is presented in 200 ml THF at RT. At 0-10° C., compound 2 (10.0 g) is carefully added in 70 ml THF. It is stirred for 30 min at RT.

Preparation: Add preparation to 300 ml ice water (exothermic, H2 development). Add 150 ml MTBE and then 150 ml 25% sulfuric acid until the precipitate (Al(OH)$_3$) slowly dissolves, separate phases, extract aqueous phase 2× with 50 ml MTBE each, wash combined organic phases 1× with 100 ml soda solution and 1× with 100 ml saturated NaCl solution, dry over Na$_2$SO$_4$ and concentrate. The raw product (10.0 g) is fractionally distilled under vacuum at (60° C./500-10 mbar) using a Vigreux column.

Yield: 9.5 g (94%)

trans-isomer: NMR: $^1$H-NMR (400 MHz, CDCl$_3$) δ 4.09-4.01 (m, 1H), 1.78-1.57 (m, 5H), 1.56-1.45 (m, 3H), 1.25 (ddd, J=13.3, 10.5, 2.9 Hz, 1H), 1.21-1.15 (m, 4H), 1.04-0.92 (m, 1H), 0.86 (d, J=6.6 Hz, 6H)

$^{13}$C-NMR (101 MHz, CDCl$_3$) δ 67.08 (CH), 39.97 (CH$_2$), 36.41 (CH$_2$), 34.26 (CH$_2$), 33.61 (CH$_2$), 32.35 (CH$_2$), 31.97 (CH), 28.36 (CH), 22.81 (CH$_3$), 22.81 (CH$_3$), 20.21 (CH$_2$).

cis isomer: NMR: $^1$H-NMR (400 MHz, CDCl$_3$) δ 3.55 (tt, J=10.8, 4.2 Hz, 1H), 2.03-1.93 (m, 2H), 1.76 (dp, J=12.9, 3.2 Hz, 1H), 1.69-1.61 (m, 1H), 1.55-1.42 (m, J=6.5 Hz, 1H), 1.33-1.17 (m, 6H), 1.16-1.07 (m, 1H), 0.93-0.83 (m, 1H), 0.87 (d, J=6.6 Hz, 6H), 0.77 (tdd, J=12.6, 10.9, 3.5 Hz, 1H)

$^{13}$C-NMR (101 MHz, CDCl$_3$) δ 71.14 (CH), 42.93 (CH$_2$), 36.90 (CH), 36.35 (CH$_2$), 36.06 (CH$_2$), 34.91 (CH$_2$), 32.35 (CH$_2$), 28.36 (CH), 24.33 (CH$_2$), 22.83 (CH$_3$) 22.81 (CH$_3$).

Example 3: (3 E/Z)-1-Isopentyl-3-(methoxymethylene)cyclohexane (4)

Prepare methoxymethyltriphenylphosphonium chloride (84.2 g, 0.246 mol) in 500 ml THF and allow to cool to 0° C., add potassium tert-butylate (112 g, 0.40 mol) in portions at 0 to 5° C. Allow to stir for 30 minutes and then slowly drop 3-isopentylcyclohexanones (27.5 g, 0.164 mol) in 100 ml THF into the reaction solution, keeping the temperature below 10° C. Allow to stir for 30 minutes at <10° C. and then slowly warm up to RT over a period of 22 h.

Preparation: Quench the preparation with H$_2$O, extract 3× with 1000 ml ethyl acetate, wash the combined organic phases with 200 ml total NaCl solution, dry and condense (60° C./500-10 mbar). The raw product (96.2 g) was distilled on a spherical tube. (150° C., 0.8 mbar).

Yield: 36.2 g (quantitative)

$^1$H-NMR (400 MHz, CDCl$_3$) δ 5.75 (d, J=1.7 Hz, 1H), 5.74 (t, J=2.0 Hz, 1H), 3.53 (s, 6H), 2.75-2.67 (m, 1H), 2.66-2.59 (m, 1H), 2.06 (dt, J=13.0, 2.3 Hz, 1H), 2.02-1.91 (m, 1H), 1.91-1.80 (m, 1H), 1.80-1.69 (m, 4H), 1.70-1.55 (m, 1H), 1.49 (dddd, J=12.8, 10.4, 6.3, 2.6 Hz, 2H), 1.43 (s, 2H), 1.40-1.11 (m, 13H), 1.10-0.94 (m, 2H), 0.94-0.81 (m, 12H).

$^{13}$C-NMR (101 MHz, CDCl$_3$) δ 138.95, 138.94$_{isomer}$, 117.98, 117.93$_{isomer}$, 59.28, 59.28$_{isomer}$, 39.44$_{isomer}$, 38.21$_{isomer}$, 37.14, 37.43, 37.14$_{isomer}$, 36.27, 36.24$_{isomer}$, 34.68, 34.51$_{isomer}$, 33.19, 31.38, 28.32, 28.30$_{isomer}$, 28.25, 28.23$_{isomer}$, 26.93$_{isomer}$, 22.70, 22.67$_{isomer}$, 22.65, 22.63$_{isomer}$.

Example 4: 3-isopentylcyclohexanecarbaldehyde (5)

Compound 4 (35.0 g, 0.178 mol) in THF (400 ml) and 10% HCl solution (96 ml) was placed in a 1l stirrer, then the educts were added one after the other and the mixture was heated to boiling temperature, heating for 1 h under reflux.

Preparation: Quench the preparation with water and extract 3× with MTBE. Wash the combined organic phases once with $H_2O$, dry and evaporate (60° C./500-10 mbar). The raw product (31.0 g) was distilled fractionated on Vigreux colons under vacuum.

Yield: 31.0 g (95%)

trans-isomer: NMR: 1H-NMR (400 MHz, $CDCl_3$) δ 9.60 (d, J=1.57 Hz, 1H), 2.23 (ttd, J=12.17, 3.52, 1.62 Hz, 1H), 1.98 (mc, 3H), 1.75 (tq, J=14.30, 3.34, 1.72 Hz, 1H), 1.71 (mc, 1H), 1.64 (mc, 3H), 1.20 (mc, 5H), 1.14 (J=3.70 Hz, 1H), 0.86 (d, J=6.73 Hz, 6H).

$^{13}$C-NMR (101 MHz, $CDCl_3$) δ 204.83, 50.64, 37.13, 36.31, 36.05, 35.05, 33.58, 28.22, 26.12, 25.44, 22.63, 22.63

Example 5: (3-isopentylcyclohexyl) Methanol (6)

Under nitrogen (rinse apparatus thoroughly), LAH (3.2 g, 0.085 mol) is presented in 200 ml THF at RT. At 0-10° C., 3-isopentyl cyclohexane carbaldehyde (14.0 g, 0.077 mol) is carefully added in 70 ml THF. It is stirred for 30 min at RT.

Preparation: Add preparation to 300 ml ice water (exothermic, H2 development). Add 150 ml MTBE to the preparation, then add 150 ml of 25% sulfuric acid until the precipitate $(Al(OH)_3)$ slowly dissolves, separate phases, extract aqueous phase twice with 50 ml MTBE each, wash combined organic phases once with 100 ml soda solution and once with 100 ml saturated NaCl solution, dry over $Na_2SO_4$, evaporate (60° C./500-10 mbar). The raw product (13.3 g) was distilled on a spherical tube still. (90° C., 1.0 mbar).

Yield: 12.7 g (90%)

$^1$H-NMR (600 MHz, $CDCl_3$) δ 3.46 (dd, J=10.5, 6.3 Hz, 1H), 3.44 (dd, J=10.6, 6.3 Hz, 1H), 1.82-1.71 (m, 3H), 1.56-1.45 (m, 2H), 1.45-1.36 (m, 2H), 1.31-1.21 (m, 2H), 1.21-1.12 (m, 3H), 0.88 (d, J=6.8 Hz, 1H), 0.86 (d, J=6.6 Hz, 6H), 0.85-0.77 (m, 2H), 0.57 (q, J=11.9 Hz, 1H);

$^{13}$C-NMR (151 MHz, $CDCl_3$) δ 68.93, 40.60, 37.50, 36.18, 35.46, 33.41, 32.77, 29.59, 28.54, 25.82, 22.71, 22.68.

Example 6: 1-isopentyl Cyclohexane Carbaldehyde (7)

Analogous to connection 3, connection 7 was established.

1H-NMR (400 MHz, $CDCl_3$) δ 9.81 (d, J=1.3 Hz, 1H), 9.55 (d, J=4.0 Hz, 1H), 2.45 (dtd, J=6.8, 3.9, 1.9 Hz, 1H), 2.01 (ddt, J=10.0, 10.1, 3.9 Hz, 1H), 1.93-1.81 (m, 4H), 1.80-1.66 (m, 3H), 1.65-1.59 (m, 4H), 1.59-1.51 (m, 3H), 1.51-1.43 (m, 2H), 1.42-1.30 (m, 5H), 1.29-1.20 (m, 4H), 1.19-1.08 (m, 3H), 0.92 (d, J=6.6 Hz, 3H), 0.87 (d, J=6.6 Hz, 3H), 0.86 (d, J=6.5 Hz, 3H), 0.84 (d, J=6.5 Hz, 3H).

$^{13}$C-NMR (101 MHz, $CDCl_3$) δ 206.13, 205.71, 70.63, 61.38, 55.81, 52.19, 51.07, 42.00, 41.96, 41.75, 37.26, 36.94, 36.72, 36.44, 35.70, 32.44, 30.34, 29.32, 28.73, 28.19, 28.14, 27.03, 26.52, 26.11, 25.27, 25.01, 24.77, 24.70, 24.21, 23.80, 23.69, 22.87, 22.71, 22.68, 22.62, 22.52, 22.28, 22.13.

Example 7: (1-isopentylcyclohexyl) Methanol (8)

Similar to connection 4, connection 8 was created from connection 7.

Yield: >90%

1H-NMR (400 MHz, $CDCl_3$) δ 3.71 (dd, J=10.8, 3.1 Hz, 1H), 3.67-3.58 (m, 3H), 1.871.64 (m, 9H), 1.64-1.44 (m, 5H), 1.04-1.29 (m, 18H), 0.84-0.89 (12H).

$^{13}$C-NMR (101 MHz, $CDCl_3$) δ 65.83, 63.35, 44.10, 42.09, 38.29, 37.08, 37.01, 35.57, 35.46, 31.57, 30.96, 29.59, 29.59, 28.83, 28.44, 28.30, 26.21, 25.97, 25.77, 23.01, 22.87, 22.87, 22.53, 22.37.

Example 8: 4-isopentyl Cyclohexane Carbaldehyde (9)

Analogous to connection 3, connection 9 was established.

1H-NMR (400 MHz, $CDCl_3$) δ 9.38 (s, 1H), 9.34-9.32 (m, 1H), 1.90-1.78 (m, 3H), 1.73-1.61 (m, 3H), 1.61-1.52 (m, 2H), 1.48-1.33 (m, 4H), 1.26-1.15 (m, 2H), 1.10-0.92 (m, 12H), 0.88 (d, J=6.6 Hz, 7H), 0.86 (d, J=6.6 Hz, 7H), 0.68-0.53 (m, 2H).

$^{13}$C-NMR (101 MHz, $CDCl_3$) δ 203.68, 202.89, 50.52, 47.39, 37.61, 36.95, 36.57, 36.48, 35.20, 34.12, 32.20, 32.20, 29.84, 29.84, 28.59, 28.54, 26.17, 26.17, 24.31, 24.31, 22.83, 22.83, 22.83, 22.83.

Example 9: (4-isopentylcyclohexyl) Methanol (10)

Similar to connection 4, connection 10 was created from connection 9.

Yield: >90%

1H-NMR (400 MHz, $CDCl_3$) δ 3.44 (d, J=6.3 Hz, 2H), 1.78 (d, J=9.1 Hz, 4H), 1.48 (ddt, J=11.4, 7.5, 4.5 Hz, 1H), 1.41 (dd, J=10.8, 5.3 Hz, 1H), 1.17 (d, J=3.1 Hz, 4H), 1.15 (d, J=3.5 Hz, 1H), 0.98-0.88 (m, 5H), 0.86 (d, J=6.6 Hz, 6H).

$^{13}$C-NMR (101 MHz, $CDCl_3$) δ 122.66, 68.83, 67.44, 66.47, 40.17, 38.44, 38.12, 36.77 36.32, 35.43, 35.11, 34.18, 33.82, 32.74, 31.83, 29.52, 28.97, 28.86, 28.28, 28.24, 25.76, 25.38, 22.70, 22.68.

Example 10: Shampoo

The compound from example 1 was incorporated into a shampoo base of the following composition in a dosage of 0.5 wt. %:

| | |
|---|---|
| Sodium lauryl ether sulfate (e.g. Texapon NSO, Cognis Deutschland GmbH) | 12% |
| Cocamidopropyl betaine (e.g. Dehyton K, Cognis Deutschland GmbH) | 2% |
| Sodium Chloride | 1.4% |
| Citric acid | 1.3% |
| phenoxyethanol, methyl, ethyl, butyl and propyl paraben | 0.5% |
| Water | 82.8% |

The pH value of the shampoo base was about 6. 100 ml of a 20 wt % aqueous shampoo solution was prepared from this. In this shampoo solution, 2 hair strands were washed together for 2 minutes and then rinsed under lukewarm running water for 20 seconds. One strand of hair was wrapped wet in aluminium foil and the second strand of hair was dried with a hair dryer. Both strands of hair were evaluated by a panel for odour. Odor description of both hair strands: highly radiant, rose-like, fruity.

Example 11: Fabric Softener

The perfume composition from example 2 (after addition of 6% by weight of the ketone from example 1) was incorporated in a dosage of 0.5% by weight into a fabric softener base compound of the following composition

| | |
|---|---|
| Quaternary ammonium methosulfate (esterquat), approx. 90 (e.g. Rewoquat WE 18, Witco Surfactants GmbH) | 5.5% |
| Alkyldimethylbenzylammonium chloride, approx. 50 (e.g. Preventol R50, Bayer AG) | 0.2% |
| color solution, approx. 1%-ig | 0.3% |
| Water | 94.0% |

The pH value of the fabric softener base was in the range of 2 to 3. Two fabric cloths were rinsed with 370 g of a 1% aqueous fabric softener solution (based on the fabric softener base containing 0.5% by weight of the perfume composition from example 2) in a Linetest machine in the fabric softener program for 30 minutes at 20° C. The rags were wrung out and then spun for 20 seconds. One cloth was wet-wrapped and one hung to dry. Afterwards, both cloths were olfactorily evaluated by a panel. Description of the odour of both fabric flaps: floral, fresh, bright and woody aspects with slight fruity sweet undertones; rounded and harmonious olfactory impression.

Example 12: Washing Powder

The perfume oil composition from example 3 (after addition of 1 wt. %) was incorporated in a washing powder base of the following formulation in a dosage of 0.4 wt. %.

| | |
|---|---|
| Linear Na-alkylbenzene sulfonate | 8.8% |
| Ethoxylated fatty alcohol C12-18 (7 EO) | 4.7% |
| Na Soap | 3.2% |
| Defoamer DOW CORNING 2-4248S POWDERED ANTIFOAM, silicone oil on zeolite as carrier material | 3.9% |
| zeolite 4A | 28.3% |
| Na-Carbonate | 11.6% |
| Na salt of a copolymer of acrylic and maleic acid (Sokalan CP5) 2.4 | |
| Na-Silicate | 3.0% |
| carboxymethyl cellulose | 1.2% |
| Dequest 2066 ([[[(phosphonomethyl)imino]bis[(ethylene nitrilo)-bis(methylene)]] tetrakis phosphonic acid, sodium salt) Optical brightener | 2.8% 0.2% |
| Na-Sulfate | 6.5% |
| protease | 0.4% |
| Sodium perborate tetrahydrate | 22.0% |
| Tetraacetylethylenediamine | 1.0% |

Two fabric cloths were washed with 370 g of a 1% aqueous washing powder lye based on the washing powder base comprising 0.4% by weight of the perfume oil composition from example 3 (the pH value of the washing powder lye is clearly in the alkaline range) in a Linetest machine in the main wash cycle for 45 minutes at 60° C. The rags were first rinsed with cold water for 5 minutes, wrung out and then spun for 20 seconds. One cloth was wet-welded and one was hung up to dry. Afterwards, both cloths were olfactory assessed by a panel.

Description of smell in each case: strong, brilliant, rose-like with natural notes and fruity undertones; rounded and harmonious olfactory impression.

Example 13: Perfume 1

| | |
|---|---|
| IONONES BETA 50% DPG | 25.00 |
| FARENAL ® 10% DPG | 10.00 |
| FLORAZON | 1.00 |
| HEXENOL CIS-3 | 1.00 |
| HEXENYL ACETATE CIS-3 | 1.00 |
| LIGUSTRAL | 5.00 |
| ALLYLAMYLGLYCOLATE | 6.00 |
| CYCLOGALBANAT ®. | 6.00 |
| MELONAL 10% DPG | 6.00 |
| DIHYDROMYRCENOL | 32.00 |
| LINALYLACETATE | 10.00 |
| OXANTHIA 50% IN TEC 10% DPG | 3.00 |
| HEXYLACETATE | 25.00 |
| ISOAMYLACETATE | 2.00 |
| ETHYLBUTYRATE | 2.00 |
| ETHYLCAPRONATE | 2.00 |
| ALDEHYDE C14 SO-CALLED | 15.00 |
| ALDEHYDE C18 SO-CALLED | 1.00 |
| DECALACTONE GAMMA | 6.00 |
| APPLE RED AROMATIC BASE | 4.00 |
| ETHYL METHYL BUTYRATE-2 | 5.00 |
| MANZANATE | 5.00 |
| ALLYLCYCLOHEXYL PROPIONATE | 5.00 |
| ALLYL HEPTYLATE | 7.00 |
| PRUNELLA TYPE BASE | 12.00 |
| FRAMBINON ® | 10.00 |
| ETHYL MALTOL 1% DPG | 10.00 |
| CYCLAMEN ALDEHYDE | 5.00 |
| CALONE 10% DPG | 6.00 |
| HELIONAL | 45.00 |
| FLORHYDRAL | 2.50 |
| FLOROSA | 25.00 |
| ETHYLLINALOOL | 50.00 |
| DIMETHYLBENZYLCARBINYL ACETATE | 8.00 |
| TERPINEOL PURE | 12.00 |
| ROSE OXIDE | 1.00 |
| PHENYLETHYL ALCOHOL | 56.00 |
| PHENOXANOL | 15.00 |
| SYMROSE ® | 1.00 |
| DAMASCON ALPHA | 1.00 |
| DAMASCONE DELTA | 1.00 |
| BENZYLACETATE | 10.00 |
| HEDION | 140.00 |
| AMYLSALICYLAT | 65.00 |
| UNDECAVERTOL | 2.50 |
| IONON ALPHA | 10.00 |
| ISOEUGENOL ACETATE | 6.00 |
| AGRUMEX LC | 30.00 |
| SANDRANOL | 6.00 |
| EVERNYL 10% DPG | 6.00 |
| AMBROX DL 10% DPG | 3.00 |
| AMBRETTOLIDE | 7.00 |
| ETHYLENE BRASSYLATE | 95.00 |
| GLOBALIDE | 50.00 |
| INDOFLOR ® CRYSTAL. 10% DPG | 5.00 |
| DIPROPYLENE GLYCOL | 119.00 |

Example 14: Perfume 2

| | |
|---|---|
| ALCOHOL C 6 KOSHER | 6.00 |
| OCTANONE-3 | 0.50 |
| HEXENOL CIS-3 | 12.00 |
| HEXENYL ACETATE CIS-3 | 8.00 |
| VERTOCITRAL | 8.00 |
| CYCLOGALBANAT ®. | 4.00 |
| FLOROPAL | 12.00 |
| MAGNOLAN | 10.00 |
| MELONA | 4.00 |
| DIHYDROMYRCENOL | 40.00 |
| CITRONITRIL | 3.00 |
| OXANTHIA 50% IN TEC | 1.00 |
| THYMOL KRIST. | 4.00 |

-continued

| | |
|---|---|
| HEXYLACETATE | 40.00 |
| ISOAMYL ACETATE 100 | 5.00 |
| PRENYLACETATE | 4.00 |
| ETHYLBUTYRATE | 5.00 |
| EXOVERT HIGH IMPACT 10% DPG | 2.00 |
| ALDEHYDE C14 SO-CALLED | 15.00 |
| DECALACTONE GAMMA | 5.00 |
| ETHYL METHYL BUTYRATE-2 | 5.00 |
| MANZANATE | 3.00 |
| ALLYLCAPRONATE | 5.00 |
| ALLYLCYCLOHEXYL PROPIONATE | 25.00 |
| ALLYL HEPTYLATE | 40.00 |
| FRUITS | 4.00 |
| ALDEHYDE C16 SO-CALLED | 2.00 |
| FRAMBINON ® | 10.00 |
| MUGETANOL | 10.00 |
| CYCLOHEXYLMAGNOL | 25.00 |
| FREESIOL/CORPS 119 | 10.00 |
| TETRAHYDROLINALOOL | 190.00 |
| DIMETHYLBENZYLCARBINYL ACETATE | 8.00 |
| DIMETHYLBENZYLCARBINYLBUTYRATE | 10.00 |
| ROSE OXIDE | 5.00 |
| PHENIRATE | 30.00 |
| SYMROSE ® | 115.00 |
| DAMASCONE DELTA | 3.00 |
| ETHYLSAFRANAT | 3.00 |
| DELPHONE | 1.00 |
| VELOUTONE | 2.00 |
| NONADIENOL-2.6 1% DPG | 8.00 |
| UNDECAVERTOL | 8.00 |
| IRIS NITRILE 10% DPG | 3.00 |
| AGRUMEX HC | 120.00 |
| ORYCLONE SPECIAL | 165.00 |
| HERBAL FLORATE | 30.00 |
| RHUBOFIX | 0.50 |
| BRAHMANOL | 5.00 |
| SANDRANOL | 45.00 |
| SYNAMBRAN ® R 50% IN IPM | 1.00 |
| GLOBALIDE | 8.00 |
| MACROLIDE ® SUPRA | 12.00 |

Example 15: Perfume 3

| | |
|---|---|
| FLOROPAL | 1.50 |
| MAGNOLAN | 12.00 |
| DIHYDROMYRCENOL | 8.00 |
| LINALYLACETATE | 25.00 |
| TERPINYLACETATE | 12.00 |
| CITRAL FF 10% DPG | 2.00 |
| CINEOL 1.4 10% DPG | 2.00 |
| ORANGE BASE COLIPA NEW | 1.00 |
| AMAROCIT | 14.00 |
| TERPINOLEN DEXTRO 10% DPG | 2.00 |
| LAVENDER OIL CLONAL CENSO | 2.00 |
| EUCALYPTOL NAT. | 6.00 |
| CARDAMOM OIL RCO | 0.80 |
| MATE SUPERESSENCE 10% DPG | 2.00 |
| BORNEOL L/ISOBORNEOL 65/35 10% DPG | 3.00 |
| CAMPHOR DL 10% IPM | 12.00 |
| SULTANENE ® 1% DPG | 5.00 |
| HELIONAL | 5.00 |
| ETHYLLINALOOL | 45.00 |
| LINALOOL OXIDE | 1.00 |
| TETRAHYDROLINALOOL | 35.00 |
| DIMETHYLBENZYLCARBINYLBUTYRATE | 1.00 |
| TERPINEOL ALPHA | 0.50 |
| PHENYLETHYL ACETATE | 0.50 |
| PHENYLETHYL ALCOHOL | 13.00 |
| PHENOXANOL | 3.00 |
| SYMROSE ® | 1.00 |
| DAMASCENON TOTAL 10% DPG | 2.00 |
| GIVESCONE | 2.00 |
| HEDION | 220.00 |
| JASMONE CIS 10% DPG | 8.00 |
| METHYLOCTINE CARBONATE 10% DPG | 1.00 |

-continued

| | |
|---|---|
| UNDECAVERTOL | 3.00 |
| ALLYLIONON | 3.00 |
| IONON ALPHA | 12.00 |
| IONON BETA | 80.00 |
| IRON ALPHA | 2.00 |
| HELIOTROPIN/PIPERONAL | 4.00 |
| COUMARONE 10% IPM | 2.00 |
| KOUMALACTONES 10% TEC 1% DPG | 4.00 |
| OCTAHYDROCOUMARIN | 4.00 |
| TONKA BEANS ABS. 10% DPG | 6.00 |
| TABANON 1% DPG | 2.00 |
| ISO E SUPER | 80.00 |
| GUAJAKHOEL | 10.00 |
| GLOBALIDE | 20.00 |
| MACROLIDE ® SUPRA | 2.00 |
| GALAXOLIDE PURE | 40.00 |
| DIPROPYLENE GLYCOL | 128.70 |

Example 16: Perfume 4

| | |
|---|---|
| IONONE BETA REPL BY DPG | 5.00 |
| VINEGAR | 1.00 |
| ALDEHYD C10 | 1.00 |
| ALDEHYDE C11 UNDECANAL | 0.50 |
| ALDEHYDE C12 LAURINE | 3.00 |
| HEXENOL CIS-3 | 5.00 |
| HEXENYL ACETATE CIS-3 | 5.00 |
| VERTOCITRAL | 5.00 |
| VERTACETAL | 0.50 |
| STYROLYLACETATE | 15.00 |
| STYROLYLPROPIONATE | 0.50 |
| ISOPROPYLMETHYLTHIAZOLE-2.4 10% DPG | 1.00 |
| MELONAL 10% DPG | 2.00 |
| DIHYDROMYRCENOL | 25.00 |
| LEMON OIL ITAL. | 5.00 |
| ORANGE OIL | 5.00 |
| AMAROCIT | 25.00 |
| CITRORANGE BASE COLIPA | 5.00 |
| MENTHOL L DIST. | 1.00 |
| ETHYLACETATE | 2.00 |
| HEXYLACETATE | 5.00 |
| ISOAMYL ACETATE 100 | 1.00 |
| ISOBUTYL ACETATE 10% DPG | 2.00 |
| JASMAPRUNAT | 2.50 |
| PRENYLACETATE | 0.50 |
| BUTYLBUTYRATE | 2.00 |
| HEXYL BUTYRATE | 3.00 |
| CAPROIC ACID NAT. | 1.00 |
| ALDEHYDE C14 SO-CALLED | 15.00 |
| DECALACTONE GAMMA | 2.00 |
| ETHYL METHYL BUTYRATE-2 | 1.50 |
| SYMFRESH ® NX | 25.00 |
| ALLYLCAPRONATE | 5.00 |
| ALLYLCYCLOHEXYL PROPIONATE | 8.00 |
| ALLYL HEPTYLATE | 4.00 |
| THIOMENTHANONE-8.3 1% TEC | 2.00 |
| ETHYLMALTOL | 5.00 |
| PASSIONFRUIT TYPE BASE | 25.00 |
| MAJANTOL | 15.00 |
| TETRAHYDROLINALOOL | 50.00 |
| DIMETHYLBENZYLCARBINYL ACETATE | 10.00 |
| ROSE OXIDE L | 1.00 |
| SYMROSE ® | 15.00 |
| DAMASCONE DELTA | 2.00 |
| BENZYLACETATE | 15.00 |
| HEDION | 150.00 |
| VELOUTONE | 1.50 |
| HEXYLSALICYLATE | 15.00 |
| UNDECAVERTOL | 2.50 |
| ISOEUGENOL ACETATE | 0.50 |
| AGRUMEX LC | 25.00 |
| ORYCLONE SPECIAL | 10.00 |
| HERBYLPROPIONATE | 2.00 |
| SANDRANOL | 25.00 |
| ETHYLENE BRASSYLATE | 25.00 |

| | |
|---|---|
| GLOBALIDE | 25.00 |
| DIPROPYLENE GLYCOL | 389.50 |

Example 17: Perfume 5

| | |
|---|---|
| IONONES BETA 50% DPG | 25.00 |
| FARENAL ® 10% DPG | 10.00 |
| FLORAZON | 1.00 |
| HEXENOL CIS-3 | 1.00 |
| HEXENYL ACETATE CIS-3 | 1.00 |
| LIGUSTRAL | 5.00 |
| ALLYLAMYLGLYCOLATE | 6.00 |
| CYCLOGALBANAT ®. | 6.00 |
| MELONAL 10% DPG | 6.00 |
| DIHYDROMYRCENOL | 32.00 |
| LINALYLACETATE | 10.00 |
| OXANTHIA 50% IN TEC 10% DPG | 3.00 |
| HEXYLACETATE | 25.00 |
| ISOAMYLACETATE | 2.00 |
| ETHYLBUTYRATE | 2.00 |
| ETHYLCAPRONATE | 2.00 |
| ALDEHYDE C14 SO-CALLED | 15.00 |
| ALDEHYDE C18 SO-CALLED | 1.00 |
| DECALACTONE GAMMA | 6.00 |
| APPLE RED AROMATIC BASE | 4.00 |
| ETHYL METHYL BUTYRATE-2 | 5.00 |
| MANZANATE | 5.00 |
| ALLYLCYCLOHEXYL PROPIONATE | 5.00 |
| ALLYL HEPTYLATE | 7.00 |
| PRUNELLA TYPE BASE | 12.00 |
| FRAMBINON ® | 10.00 |
| ETHYL MALTOL 1% DPG | 10.00 |
| CYCLAMEN ALDEHYDE | 5.00 |
| CALONE 10% DPG | 6.00 |
| HELIONAL | 45.00 |
| FLORHYDRAL | 2.50 |
| FLOROSA | 25.00 |
| ETHYLLINALOOL | 50.00 |
| DIMETHYLBENZYLCARBINYL ACETATE | 8.00 |
| TERPINEOL PURE | 12.00 |
| AMAROCIT | 1.00 |
| PHENYLETHYL ALCOHOL | 56.00 |
| PHENOXANOL | 15.00 |
| 3-(3-Methylbutyl)cyclohexan-1-one (2) | 1.00 |
| DAMASCON ALPHA | 1.00 |
| DAMASCONE DELTA | 1.00 |
| BENZYLACETATE | 10.00 |
| HEDION | 140.00 |
| AMYLSALICYLAT | 65.00 |
| UNDECAVERTOL | 2.50 |
| IONON ALPHA | 10.00 |
| ISOEUGENOL ACETATE | 6.00 |
| AGRUMEX LC | 30.00 |
| SANDRANOL | 6.00 |
| EVERNYL 10% DPG | 6.00 |
| AMBROX DL 10% DPG | 3.00 |
| AMBRETTOLIDE | 7.00 |
| ETHYLENE BRASSYLATE | 95.00 |
| GLOBALIDE | 50.00 |
| INDOFLOR ® CRYSTAL. 10% DPG | 5.00 |
| DIPROPYLENE GLYCOL | 119.00 |

Example 18: Perfume 6

| | |
|---|---|
| IONONE BETA REPL BY DPG | 5.00 |
| VINEGAR | 1.00 |
| ALDEHYD C10 | 1.00 |
| ALDEHYDE C11 UNDECANAL | 0.50 |
| ALDEHYDE C12 LAURINE | 3.00 |
| HEXENOL CIS-3 | 5.00 |
| HEXENYL ACETATE CIS-3 | 5.00 |
| VERTOCITRAL | 5.00 |
| VERTACETAL | 0.50 |
| STYROLYLACETATE | 15.00 |
| STYROLYLPROPIONATE | 0.50 |
| ISOPROPYLMETHYLTHIAZOLE-2.4 DPG 10% | 1.00 |
| MELONAL 10% DPG | 2.00 |
| DIHYDROMYRCENOL | 25.00 |
| LEMON OIL ITAL. | 5.00 |
| ORANGE OIL | 5.00 |
| AMAROCIT | 25.00 |
| CITRORANGE BASE COLIPA | 5.00 |
| MENTHOL L DIST. | 1.00 |
| ETHYLACETATE | 2.00 |
| HEXYLACETATE | 5.00 |
| ISOAMYL ACETATE 100 | 1.00 |
| ISOBUTYL ACETATE 10% DPG | 2.00 |
| JASMAPRUNAT | 2.50 |
| PRENYLACETATE | 0.50 |
| BUTYLBUTYRATE | 2.00 |
| HEXYL BUTYRATE | 3.00 |
| CAPROIC ACID NAT. | 1.00 |
| ALDEHYDE C14 SO-CALLED | 15.00 |
| DECALACTONE GAMMA | 2.00 |
| ETHYL METHYL BUTYRATE-2 | 1.50 |
| SYMFRESH ® NX | 25.00 |
| ALLYLCAPRONATE | 5.00 |
| ALLYLCYCLOHEXYL PROPIONATE | 8.00 |
| ALLYL HEPTYLATE | 4.00 |
| THIOMENTHANONE-8.3 1% TEC | 2.00 |
| ETHYLMALTOL | 5.00 |
| PASSIONFRUIT TYPE BASE | 25.00 |
| MAJANTOL | 15.00 |
| TETRAHYDROLINALOOL | 50.00 |
| DIMETHYLBENZYLCARBINYL ACETATE | 10.00 |
| DAMASCON ALPHA | 1.00 |
| 3-(3-Methylbutyl) cyclohexan-1-one (2) | 15.00 |
| DAMASCONE DELTA | 2.00 |
| BENZYLACETATE | 15.00 |
| HEDION | 150.00 |
| VELOUTONE | 1.50 |
| HEXYLSALICYLATE | 15.00 |
| UNDECAVERTOL | 2.50 |
| ISOEUGENOL ACETATE | 0.50 |
| AGRUMEX LC | 25.00 |
| ORYCLONE SPECIAL | 10.00 |
| HERBYLPROPIONATE | 2.00 |
| SANDRANOL | 25.00 |
| ETHYLENE BRASSYLATE | 25.00 |
| GLOBALIDE | 25.00 |
| DIPROPYLENE GLYCOL | 389.50 |

Example 19: Perfume 7

| | |
|---|---|
| IONONE BETA REPL BY DPG | 5.00 |
| VINEGAR | 1.00 |
| ALDEHYD C10 | 1.00 |
| ALDEHYDE C11 UNDECANAL | 0.50 |
| ALDEHYDE C12 LAURINE | 3.00 |
| HEXENOL CIS-3 | 5.00 |
| HEXENYL ACETATE CIS-3 | 5.00 |
| VERTOCITRAL | 5.00 |
| VERTACETAL | 0.50 |
| STYROLYLACETATE | 15.00 |
| STYROLYLPROPIONATE | 0.50 |
| ISOPROPYLMETHYLTHIAZOLE-2.410% DPG | 1.00 |
| MELONAL 10% DPG | 2.00 |
| DIHYDROMYRCENOL | 25.00 |
| LEMON OIL ITAL. | 5.00 |
| ORANGE OIL | 5.00 |
| AMAROCIT | 25.00 |
| CITRORANGE BASE COLIPA | 5.00 |
| MENTHOL L DIST. | 1.00 |
| ETHYLACETATE | 2.00 |
| HEXYLACETATE | 5.00 |

-continued

| | |
|---|---|
| ISOAMYL ACETATE 100 | 1.00 |
| ISOBUTYL ACETATE 10% DPG | 2.00 |
| JASMAPRUNAT | 2.50 |
| PRENYLACETATE | 0.50 |
| BUTYLBUTYRATE | 2.00 |
| HEXYL BUTYRATE | 3.00 |
| CAPROIC ACID NAT. | 1.00 |
| ALDEHYDE C14 SO-CALLED | 15.00 |
| DECALACTONE GAMMA | 2.00 |
| ETHYL METHYL BUTYRATE-2 | 1.50 |
| SYMFRESH?+0 NX | 25.00 |
| ALLYLCAPRONATE | 5.00 |
| ALLYLCYCLOHEXYL PROPIONATE | 8.00 |
| ALLYL HEPTYLATE | 4.00 |
| THIOMENTHANONE-8.3 1% TEC | 2.00 |
| ETHYLMALTOL | 5.00 |
| PASSIONFRUIT TYPE BASE | 25.00 |
| MAJANTOL | 15.00 |
| TETRAHYDROLINALOOL | 50.00 |
| DIMETHYLBENZYLCARBINYL ACETATE | 10.00 |
| 3-(3-Methylbutyl) cyclohexan-1-ol (3) | 1.00 |
| (4-ISOP ENTYLCYCLOH EXYL)M ETHANOL | 15.00 |
| DAMASCONE DELTA | 2.00 |
| BENZYLACETATE | 15.00 |
| HEDION | 150.00 |
| VELOUTONE | 1.50 |
| HEXYLSALICYLATE | 15.00 |
| UNDECAVERTOL | 2.50 |
| ISOEUGENOL ACETATE | 0.50 |
| AGRUMEX LC | 25.00 |
| ORYCLONE SPECIAL | 10.00 |
| HERBYLPROPIONATE | 2.00 |
| SANDRANOL | 25.00 |
| ETHYLENE BRASSYLATE | 25.00 |
| GLOBALIDE | 25.00 |
| DIPROPYLENE GLYCOL | 389.50 |

Example 20: Perfume 8

| | |
|---|---|
| IONONES BETA 50% DPG | 25.00 |
| FARENAL ® 10% DPG | 10.00 |
| FLORAZON | 1.00 |
| HEXENOL CIS-3 | 1.00 |
| HEXENYL ACETATE CIS-3 | 1.00 |
| LIGUSTRAL | 5.00 |
| ALLYLAMYLGLYCOLATE | 6.00 |
| CYCLOGALBANAT ®. | 6.00 |
| MELONAL 10% DPG | 6.00 |
| DIHYDROMYRCENOL | 32.00 |
| LINALYLACETATE | 10.00 |
| OXANTHIA 50% IN TEC 10% DPG | 3.00 |
| HEXYLACETATE | 25.00 |
| ISOAMYLACETATE | 2.00 |
| ETHYLBUTYRATE | 2.00 |
| ETHYLCAPRONATE | 2.00 |
| ALDEHYDE C14 SO-CALLED | 15.00 |
| ALDEHYDE C18 SO-CALLED | 1.00 |
| DECALACTONE GAMMA | 6.00 |
| APPLE RED AROMATIC BASE | 4.00 |
| ETHYL METHYL BUTYRATE-2 | 5.00 |
| MANZANATE | 5.00 |
| ALLYLCYCLOHEXYL PROPIONATE | 5.00 |
| ALLYL HEPTYLATE | 7.00 |
| PRUNELLA TYPE BASE | 12.00 |
| FRAMBINON ® | 10.00 |
| ETHYL MALTOL 1% DPG | 10.00 |
| CYCLAMEN ALDEHYDE | 5.00 |
| CALONE 10% DPG | 6.00 |
| HELIONAL | 45.00 |
| FLORHYDRAL | 2.50 |
| FLOROSA | 25.00 |
| ETHYLLINALOOL | 50.00 |
| DIMETHYLBENZYLCARBINYL ACETATE | 8.00 |
| TERPINEOL PURE | 12.00 |
| 3-(3-Methylbutyl) cyclohexan-1-ol (3) | 1.00 |

-continued

| | |
|---|---|
| PHENYLETHYL ALCOHOL | 56.00 |
| PHENOXANOL | 15.00 |
| (1-ISOPENTYLCYCLOHEXYL)METHANOL | 1.00 |
| DAMASCON ALPHA | 1.00 |
| DAMASCONE DELTA | 1.00 |
| BENZYLACETATE | 10.00 |
| HEDION | 140.00 |
| AMYLSALICYLAT | 65.00 |
| UNDECAVERTOL | 2.50 |
| IONON ALPHA | 10.00 |
| ISOEUGENOL ACETATE | 6.00 |
| AGRUMEX LC | 30.00 |
| SANDRANOL | 6.00 |
| EVERNYL 10% DPG | 6.00 |
| AMBROX DL 10% DPG | 3.00 |
| AMBRETTOLIDE | 7.00 |
| ETHYLENE BRASSYLATE | 95.00 |
| GLOBALIDE | 50.00 |
| INDOFLOR ® CRYSTAL. 10% DPG | 5.00 |
| DIPROPYLENE GLYCOL | 119.00 |

All perfume examples show fruity scent mixtures. The perfume examples 5 to 8 are characterized by particularly intensified fruity notes.

The invention claimed is:
1. A method comprising using a compound of formula (Ib),

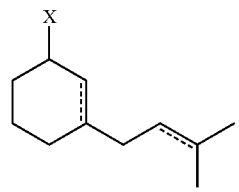

Formula (Ib)

where
X represents an —OH group,
at the respective location of one of the dotted lines there is a single bond or a double bond, and wherein at least one double bond is present
as a fragrance and/or flavour substance.
2. The method according to claim 1, wherein the fragrance is a rose note fragrance.
3. The method according to claim 1, comprising using the compound of formula (I) for imparting, modifying and/or enhancing one, two or more olfactory notes selected from the group consisting of the notes green, herbaceous, fresh, fruity, floral, woody, sweet, earthy, greasy, metallic and balsamic.
4. A fragrance and/or flavour composition, the fragrance and/or flavour composition comprising at least one compound of formula (Ib),

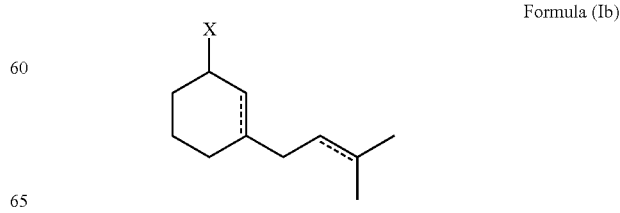

Formula (Ib)

where
X represents an —OH group,
at the respective location of one of the dotted lines there is a single bond or a double bond, wherein at least one double bond is present.

5. A fragrance and/or flavour mixture, the fragrance and/or flavour mixture comprising at least one fragrance and/or flavour composition according to claim 4, and
further comprising one or more additional fragrances and/or flavouring substances, wherein the additional or one, more or all fragrances and/or flavouring substances are selected from the group consisting of: extracts from natural raw materials, essential oils, creams, absolutes, resins, resinoids, balms, tinctures and/or single fragrance substances; and mixtures thereof.

6. A fragrance and/or flavour composition, the fragrance and/or flavour composition comprising:
(a) at least one of one or more compounds of the formula (Ib),

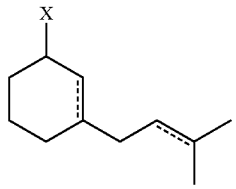

Formula (Ib)

where
X represents an —OH group,
at the respective location of one of the dotted lines there is a single bond or a double bond, wherein at least one double bond is present, and
(b) one or more other fragrance and/or flavour substances.

7. A fragrance and/or flavour composition according to claim 6,
wherein the one or more further fragrance and/or flavour substance(s) is/are selected from the group consisting of: ethyl 2-cyclopent-2-en-1-yl acetate, 1-cyclohexylethyl (E)-but-2-enoate, (2-cyclopentylcyclopentyl) (E)-but-2-enoate, allyl hexanoate, 1,3-dimethylbutyl (E)-but-2-enoate, 1,3-dimethylbut-3-enyl 2-methyl propanoate, and (E)-1-(2,6,6-trimethylcyclohex-2-en-1-yl)but-2-en-1-one.

8. A perfumed or flavoured article, the perfumed or flavoured article comprising
(a) at least one of one or more compounds of the formula (Ib),

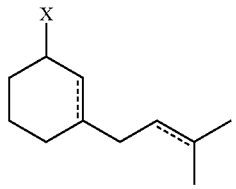

Formula (Ib)

where
X represents an —OH group,
at the respective location of one of the dotted lines there is a single bond or a double bond, wherein at least one double bond is present, (b) one, two, three, four, five, six, seven, eight, nine, ten or more further fragrance and/or flavour substances; and
(c) one or more further additives, excipients and/or active substances.

9. A perfumed or flavoured article according to claim 8, wherein the perfumed or flavoured article is selected from the group consisting of:
perfume extracts, eau de parfums, eau de toilettes, after-shave lotions, eau de colognes, pre-shave products, splash colognes, perfumed refreshing tissues, acid, alkaline or neutral detergents, textile fresheners, ironing aids, liquid detergents, powder detergents, laundry pre-treatment products, fabric softeners, laundry soaps, washing tablets, disinfectants, surface disinfectants, air fresheners, aerosol sprays, waxes and polishes, personal care products, hand creams and lotions, foot creams and lotions, depilatory creams and lotions, after-shave creams and lotions, tanning creams and lotions, hair care products, deodorants, antiperspirants, decorative cosmetic products, candles, lamp oils, incense sticks, insecticides, repellents and fuels.

10. A perfumed or flavoured article according to claim 8, wherein the total amount of compounds of formula (I), and/or 2-(3-methylbutyl)cyclohexan-1-ol, and/or 2-(3-methylbutyl)cyclohexan-1-one, and/or 3-(3-methylbutyl)cyclohexan-1-ol, and/or 3-(3-methylbutyl)cyclohexan-1-one, and/or 4-(3-methylbutyl)cyclohexan-1-one is in the range from 0.00001 to 10 wt. % based on the total mass of the article.

11. The method of claim 1, wherein the compound of formula (Ib) is selected from

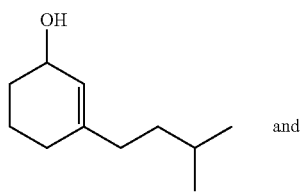

and

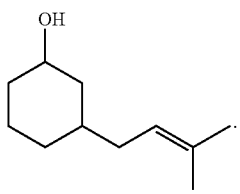

.

12. The fragrance and/or flavour composition of claim 4, wherein the compound of formula (Ib) is selected from

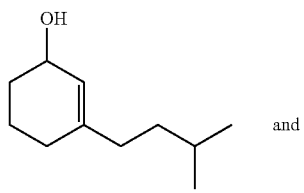

and

-continued

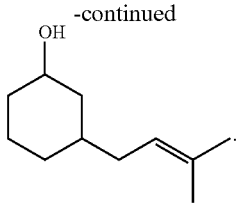

13. The fragrance and/or flavour composition of claim 6, wherein the compound of formula (Ib) is selected from

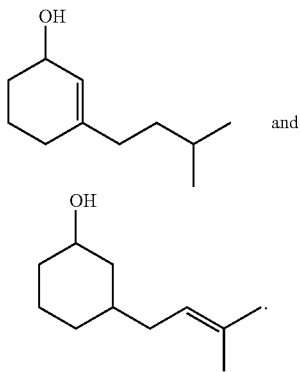

14. The perfumed or flavoured article of claim 8, wherein the compound of formula (Ib) is selected from

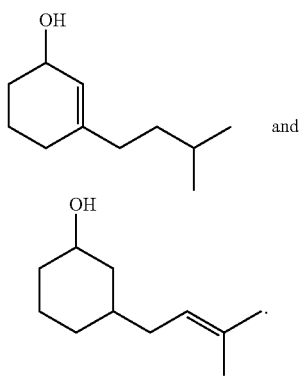

15. The fragrance and/or flavor composition according to claim 6, further comprising one or more compounds selected from the group consisting of 2-(3-methylbutyl)cyclohexan-1-ol, 2-(3-methylbutyl)cyclohexan-1-one, 3-(3-methylbutyl)cyclohexan-1-ol, 3-(3-methylbutyl)cyclohexan-1-one, 4-(3-methylbutyl)cyclohexan-1-ol, and 4-(3-methylbutyl)cyclohexan-1-one.

16. The perfumed or flavored article of claim 8, further comprising one or more compounds selected from the group consisting of 2-(3-methylbutyl)cyclohexan-1-ol, 2-(3-methylbutyl)cyclohexan-1-one, 3-(3-methylbutyl)cyclohexan-1-ol, 3-(3-methylbutyl)cyclohexan-1-one, 4-(3-methylbutyl)cyclohexan-1-ol, and 4-(3-methylbutyl)cyclohexan-1-one.

* * * * *

UNITED STATES PATENT AND TRADEMARK OFFICE
CERTIFICATE OF CORRECTION

PATENT NO. : 11,634,659 B2
APPLICATION NO. : 17/261444
DATED : April 25, 2023
INVENTOR(S) : Bernd Hoelscher et al.

Page 1 of 1

It is certified that error appears in the above-identified patent and that said Letters Patent is hereby corrected as shown below:

In the Claims

Column 46, Line 48, "formula (I)" should read "formula (Ib)".

Column 48, Line 26, "formula (I)" should read "formula (Ib)".

Signed and Sealed this
Fifteenth Day of August, 2023

Katherine Kelly Vidal
*Director of the United States Patent and Trademark Office*